United States Patent [19]

Ackermann et al.

[11] Patent Number: 5,420,301

[45] Date of Patent: May 30, 1995

[54] PROCESS FOR THE PREPARATION OF SUBSTITUTED DIFLUOROBENZO-1,3-DIOXOLES

[75] Inventors: Peter Ackermann, Pfeffingen; Hans-Ruedi Känel, Bubendorf; Bruno Schaub, Courroux, all of Switzerland

[73] Assignee: Ciba-Geigy Corporation, Ardsley, N.Y.

[21] Appl. No.: 147,617

[22] Filed: Nov. 5, 1993

Related U.S. Application Data

[60] Division of Ser. No. 987,902, Dec. 4, 1992, Pat. No. 5,281,718, which is a division of Ser. No. 583,787, Sep. 14, 1990, Pat. No. 5,194,628, and a continuation-in-part of Ser. No. 321,939, Mar. 10, 1989, abandoned.

[30] Foreign Application Priority Data

Mar. 18, 1988 [CH] Switzerland ............... 1044/88
Mar. 18, 1988 [CH] Switzerland ............... 1052/88

[51] Int. Cl.⁶ ............... C07D 317/50; C07D 317/52; C07D 317/54
[52] U.S. Cl. .................... 549/213; 549/214; 549/430; 549/437; 549/441; 549/445; 549/447
[58] Field of Search ............ 549/213, 214, 436, 437, 549/441, 445, 447

[56] References Cited

U.S. PATENT DOCUMENTS

| | | | |
|---|---|---|---|
| 4,502,882 | 3/1985 | Carter | 549/445 |
| 4,705,800 | 11/1987 | Nyfeler et al. | 514/422 |
| 4,722,935 | 2/1988 | Ehrenfreund | 549/441 |
| 4,780,551 | 10/1988 | Nyfeler et al. | 549/442 |
| 4,886,816 | 12/1989 | Franckowiak et al. | 514/422 |
| 4,912,229 | 3/1990 | Wollweber | 549/445 |
| 4,923,994 | 5/1990 | Wollweber | 549/445 |
| 4,925,840 | 5/1990 | Nyfeler et al. | 514/228.2 |

FOREIGN PATENT DOCUMENTS

| | | | |
|---|---|---|---|
| 0293711 | 12/1988 | European Pat. Off. | 514/422 |
| 2819788 | 11/1979 | Germany | 549/422 |
| 2927480 | 1/1980 | Germany | 549/442 |
| 3642256 | 6/1987 | Germany | 549/441 |
| 3601285 | 7/1987 | Germany | 549/422 |

OTHER PUBLICATIONS

J. Org. Chem, vol. 37, No. 4, 1972, p. 673.
Synthesis Heterocyclic Compounds, pp. 957–986, 1983.
CA111:153617S Preparation, ... microbicides. Ackermann, et al, p. 703, 1989.
CA114:101724s Preparation, ... fungicides. Sutter, p. 721, 1991.
CA 107:176019e Manufacture of ... fungicides. Kohl et al., p. 724, 1987.
CA 111:7416j Preparation of ... regulators, Daum et al., p. 713, 1989.
CA111:77991s Preparation of ... therefrom, Ehrenfreund, p. 753, 1989.
CA 118:6861h Process for ... fungicides. Knueppel et al., p. 729, 1993.
Advanced Organic Chemistry, 2nd Ed., Mar. pp. 554–557, 566–569, 1977.
J. Org. Chemistry vol. 37, No. 4, Stogryn, A New Synthesis of 3,4–(Difluoromethylenedioxy)benzaldehyde, 1972, p. 673.

Primary Examiner—Mary O. Lee
Assistant Examiner—Joseph K. McKane
Attorney, Agent, or Firm—Marla J. Mathias

[57] ABSTRACT

The reaction of 2,2-difluorobenzo-1,3-dioxole with (a) an alkali metal or an alkali metal compound and then (b) a compound $R^1-Z^1$ in which $Z^1$ is a leaving group, or with an aldehyde produces compounds of formula I

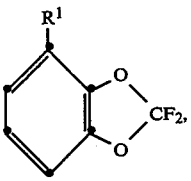

(I)

wherein $R^1$ is —OH, —SH, —CHO, —CN, —COOH, —B(OH)$_2$, —COX, with X being Cl or Br, or is —COOR$^2$, —SiR$_3^2$ or —B(OR$^2$)$_2$, with $R^2$ being a $C_1$–$C_{12}$alcohol moiety without the hydroxy group, wherein $R^1$ is further —C$_n$H$_{2n}$COOR$^2$, with n being an (Abstract continued on next page.)

integer from 1 to 4, or linear or branched $C_1$-$C_{12}$hydroxyalkyl which is unsubstituted or is substituted by —F, —CN, $C_1$-$C_6$alkoxy, phenyl, fluorophenyl, $C_1$-$C_4$alkoxy-phenyl, $C_1$-$C_4$alkylthio-phenyl, $C_1$-$C_4$alkylphenyl, $C_1$-$C_4$fluoroalkyl-phenyl, nitrophenyl or by cyanophenyl, or wherein $R^1$ is a benzyl alcohol which is unsubstituted or is substituted by F, $C_1$-$C_4$alkoxy, $C_1$-$C_4$alkylthio, $C_1$-$C_4$alkyl, $C_1$-$C_4$fluoroalkyl, nitro or by cyano, or is $C_1$-$C_{12}$acyl, or wherein $R^1$ is a radical of formula II

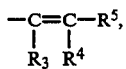 (II)

wherein $R^5$ is —CN, —$CF_3$, —$COOR^2$, —$CONH^2$, —CO—$NHR^2$ or —$CONR_2^2$, $R^3$ and $R^4$ are a direct bond or each is H, or $R^3$ is H and $R^4$ independently has the meanings of $R^5$, or $R^3$ and $R^4$ together are —$CH_2$—$NR^6$—$CH_2$—, —$CH_2$—$NR^6$—CO— or —CO—$NR^6$—CO— wherein $R^6$ is the radical of a removable protecting group, or wherein further $R^1$ is a radical of formula III

 (III)

Insecticides or fungicides can be prepared from the compounds of formula I.

3-(2,2-difluorobenzodioxol-4-yl)-4-cyanopyrrole can be prepared by reacting 4-metallo-2,2-difluorobenzodioxole (III) with an unsaturated nitrile and then with a sulfonylmethyl isocyanide in a one-pot process. The compounds III are novel intermediates.

21 Claims, No Drawings

PROCESS FOR THE PREPARATION OF SUBSTITUTED DIFLUOROBENZO-1,3-DIOXOLES

This is a divisional of Ser. No. 987,902, filed Dec. 4, 1992, now U.S. Pat. No. 5,281,718, issued Jan. 25, 1994, which in turn is a divisional of Ser. No. 583,787, filed Sep. 14, 1990, now U.S. Pat. No. 5,194,628, issued Mar. 16, 1993, which in turn is a continuation-in-part of Ser. No. 321,939, filed Mar. 10, 1989, now abandoned.

The invention relates to a process for the preparation of 2,2-difluorobenzo-1,3-dioxoles that are substituted in the 4-position, by reaction of 2,2-difluorobenzo-1,3-dioxole with an alkali metal or with an alkali metal or alkaline earth metal compound and subsequent reaction with an aldehyde or a compound having a leaving group, and to novel 2,2-difluorobenzo-1,3-dioxoles that are substituted in the 4-position.

EP-A-0 206 999 describes unsubstituted or N-substituted 3-(2,2-difluorobenzo-1,3-dioxol-4-yl)-4-cyanopyrroles which are valuable agents for controlling microorganisms. The compounds are prepared by a multi-stage synthesis. The 3-(2,2-difluorobenzo-1,3-dioxol-4-yl)-2-propenoic acid nitrile which is required as starting material is obtained by diazotisation of 4-amino-2,2-difluorobenzo-1,3-dioxole, subsequent reaction with acrylonitrile in the presence of CuCl and HCl elimination from the resulting 4-(2-chloro-2-cyano-eth-1-yl)-2,2-difluorobenzo-1,3-dioxole. (2,2-Difluorobenzo-1,3-dioxol-4-yl)-methyl esters of pyrethroid or pyrethroid-like carboxylic acids, for example, are described as insecticides in DE-OS 2 819 788. The benzodioxolylmethyl alcohols are in this case prepared by customary methods, for example with the reduction of aldehydes. 2,2-Difluorobenzo-1,3-dioxol-4-yl-carbaldehyde, however, is not mentioned.

In J. Org. Chem., Vol. 37, page 673 (1972), E. L. Stogryn describes the preparation of 2,2-difluorobenzo-1,3-dioxole-5-carbaldehyde by formylation of 2,2-difluorobenzo-1,3-dioxol-5-yllithium with dimethylformamide. The lithium compound is obtained by reaction of 1 mole 5-bromo-2,2-difluorobenzo-1,3-dioxole with 1.3 mole butyllithium. Ortho-metallation is not mentioned by Stogryn, although butyllithium was applied in 30% excess.

S. Cabiddu et al. describe in Journal of Organometallic Chemistry 136 139–146 (1977) two competitive reactions which occur by the treatment of 1,3-benzodioxole in hexane with n-butyllithium in diethyl ether/hexane at −10° C. After carbonation of the reaction mixture the authors detected the formation of 1,3-benzodioxole-4-carbonic acid, originated from the 4-lithium compound with a yield of 41% and in addition thereto pyrocatechol and n-nonane, as a result of cleavage of the ether bond with a yield of each 45% of theory.

In Synthesis, 1983, 957–984, Narasimhan and R. S. Mali describe the favourable influence of the presence of complex-forming amines, e.g. of tetramethylethylenediamine on the reactions with intermediary aromatic lithium compounds.

It has now been found that 2,2-difluorobenzo-1,3-dioxole that is free of halogen at the benzene nucleus can be reacted with alkali metals or alkali metal or alkaline earth metal compounds directly and with high specificity with regard to position to give 2,2-difluorobenzo-1,3-dioxole metallated in the 4-position which can be reacted further with electrophilic compounds to give corresponding benzenes substituted in the 4-position.

It has also been found that the optimum selectivity of the desired reaction sequence can be obtained either by adding a prepared complex of the metallating reagent to the solution of 2,2-difluoro-1,3-benzodioxole or by adding the metallating reagent to a prepared solution of the complex-forming compound and of 2,2-difluoro-1,3-benzodioxole, in both cases the molar ratio of the metallating reagent to 2,2-difluoro-1,3-benzodioxole being not more than 1.02.

The present invention relates to a process for the preparation of compounds of formula I

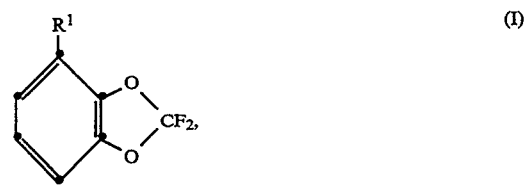

wherein $R^1$ is —OH, —SH, —CHO, —CN, —COOH, —B(OH)$_2$, —COX, with X being Cl or Br, or is —COOR$^2$, —SiR$_3{}^2$ or —B(OR$^2$)$_2$, with $R^2$ being a $C_1$-$C_{12}$alcohol moiety without the hydroxy group, wherein $R^1$ is further —C$_n$H$_{2n}$COOR$^2$, with n being an integer from 1 to 4, or linear or branched $C_1$-$_{12}$hydroxyalkyl which is unsubstituted or is substituted by —F, —CN, $C_1$-$C_6$alkoxy, phenyl, fluorophenyl, $C_1$-$C_4$alkoxy-phenyl, $C_1$-$C_4$alkylthio-phenyl, $C_1$-$C_4$alkyl-phenyl, $C_1$-$C_4$fluoroalkyl-phenyl, nitrophenyl or by cyanophenyl, or wherein $R^1$ is a benzyl alcohol or a $C_1$-$C_{12}$acyl moiety, each unsubstituted or substituted by F, $C_1$-$C_4$alkoxy, $C_1$-$C_4$alkylthio, $C_1$-$C_4$alkyl, $C_1$-$C_4$fluoroalkyl, nitro or by cyano, or wherein $R^1$ is a radical of formula II

wherein $R^5$ is —CN, —CF$_3$, —COOR$^2$, —CONH$_2$, —CO—NHR$^2$ or —CONR$_2{}^2$, $R^3$ and $R^4$ are a direct bond or each is H, or $R^3$ is H and $R^4$ independently has the meanings of $R^5$, or $R^3$ and $R^4$ together are —CH$_2$—NR$^6$—CH$_2$—, —CH$_2$—NR$^6$—CO— or —CO—NR$^6$—CO— wherein $R^6$ is the radical of a removable protecting group, or wherein further $R^1$ is a radical of formula III

which process comprises a) in an inert solvent, reacting 2,2-difluorobenzo-1,3-dioxole with an alkali metal or with an alkali metal or alkaline earth metal compound with a strong anion base to give a compound of formula IV

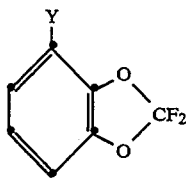 (IV)

wherein Y is an alkali metal or an alkaline earth metal, and optionally then reacting with an anhydrous metal halide from the group $MgZ_2$, $ZnZ_2$, $CdZ_2$, $CuZ$, $CuZ_2$, $PdZ_2$, $NiZ_2$, $AlZ_3$, $SiZ_4$, $SnZ_2$, $SnZ_4$, $TiZ_4$, $BZ_3$ or $ZrZ_4$ to give a compound of formula IV wherein Y is —Cu, —MgZ, —ZnZ, —CdZ, —CuZ, —PdZ, —NiZ, —$AlZ_2$, —$SiZ_3$, —SnZ, —$SnZ_3$, —$TiZ_3$, —$BZ_2$ or —$ZrZ_3$ and Z is —Cl, —Br or —I and, in the case of boron, is also —$OC_1$-$C_4$alkyl or —O-aryl, b) reacting the compound of formula IV with an electrophilic compound from the group X—CN, $CO_2$, $S_8$, $COX_2$, $B(OR^2)_3$, X—$SIR_3^2$, $R^2O$—$SiR_3^2$ or $XCOOR^2$, with X being —Cl or —Br, or with a formylating reagent, $CH_2O$, an epoxide, a benzaldehyde which is unsubstituted or is substituted by F, $C_1$-$C_4$alkoxy, $C_1$-$C_4$alkylthio, $C_1$-$C_4$alkyl, $C_1$-$C_4$fluoroalkyl, nitro or by cyano, a $C_1$-$C_{11}$alkyl—CHO which is unsubstituted or is substituted by —F, —Cl, —CN, $C_1$-$C_6$alkoxy, phenyl, fluorophenyl, $C_1$-$C_4$alkoxyphenyl, $C_1$-$C_4$alkylthiophenyl, $C_1$-$C_4$alkylphenyl, $C_1$-$C_4$fluoroalkylphenyl, nitrophenyl or by cyanophenyl, or with $C_1$-$C_{12}$acyl-$X^1$ or $C_1$-$C_{12}$fluoroacyl-$X^1$ wherein $X^1$ is —Cl, —Br, $C_1$-$C_6$alkoxy or the radical of a secondary amine, or with $X^2C_nH_{2n}COOR^2$, $X^2$—$CR^3$=$CR^4R^5$ or a compound of formula IIIa

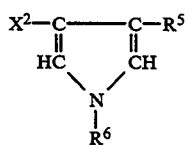 (IIIa)

wherein $X^2$ is a leaving group, and c) isolating the compound of formula I or first hydrolysing the reaction mixture and then isolating the compound of formula I.

A preferred process is that for the preparation of compounds of formula I

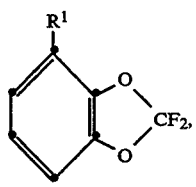 (I)

wherein $R^1$ is —CHO, —CN, —COOH, —$B(OH)_2$, —COX, with X being Cl or Br, or is —$COOR^2$ or —$B(OR^2)_2$, with $R^2$ being a $C_1$-$C_{12}$-alcohol moiety without the hydroxy group, wherein $R^1$ is further —$C_nH_{2n}COOR^2$, with n being an integer from 1 to 4, or linear or branched $C_1$-$C_{12}$hydroxyalkyl or $C_1$-$C_{12}$acyl each unsubstituted or substituted by —F, —CN, $C_1$-$C_6$alkoxy, phenyl, fluorophenyl, $C_1$-$C_4$alkoxyphenyl, $C_1$-$C_4$alkylthiophenyl, $C_1$-$C_4$alkylphenyl, $C_1$-$C_4$fluoroalkylphenyl, nitrophenyl or by cyanophenyl, or wherein $R^1$ is a radical of formula II

 (II)

wherein $R^5$ is —CN, —$CF_3$, —$COOR^2$, —$CONH_2$, —$CONHR^2$ or —$CONR_2^2$, $R^3$ and $R^4$ are a direct bond or each is H, or $R^3$ is H and $R^4$ independently has the meanings of $R^5$, or $R^3$ and $R^4$ together are —$CH_2$—$NR^6$—$CH_2$—, —$CH_2$—$NR^6$—CO— or —CO—$NR^6$—CO— wherein $R^6$ is the radical of a removable protecting group, or wherein further $R^1$is a radical of formula III

 (III)

which process comprises a) in an inert solvent, reacting 2,2-difluorobenzo-1,3-dioxole with an alkali metal or with an alkali metal or alkaline earth metal compound with a strong anion base to give a compound of formula IV

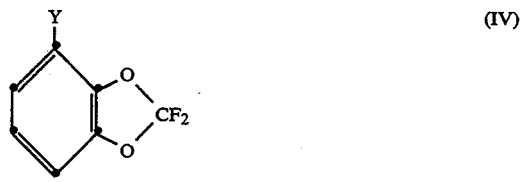 (IV)

wherein Y is an alkali metal or an alkaline earth metal, and optionally then reacting with an anhydrous metal halide from the group $MgZ_2$, $ZnZ_2$, $CdZ_2$, $CuZ$, $CuZ_2$, $PdZ_2$, $NiZ_2$, $AlZ_3$, $SiZ_4$, $SnZ_2$, $SnZ_4$, $TiZ_4$, $BZ_3$ or $ZrZ_4$ to give a compound of formula IV wherein Y is —Cu, —MgZ, —ZnZ, —CdZ, —CuZ, —PdZ, —NiZ, —$AlZ_2$, —$SiZ_3$, —SnZ, —$SnZ_3$, —$TiZ_3$, —$BZ_2$ or —$ZrZ_3$ and Z is —Cl, —Br, or —I and, in the case of boron, is also —O—$C_1$-$C_4$alkyl, b) reacting the compound of formula IV with an electrophilic compound from the group X—CN, $CO_2$, $B(OR^2)_3$, $COX_2$ or $XCOOR^2$, with X being —Cl or —Br, or with a formylating reagent, $CH_2O$, an epoxide, a $C_1$-$C_{11}$alkyl-CHO which is unsubstituted or is substituted by —F, —Cl, —CN, $C_1$-$C_6$alkoxy, phenyl, fluorophenyl, $C_1$-$C_4$alkoxyphenyl, $C_1$-$C_4$-alkylthiophenyl, $C_1$-$C_4$alkylphenyl, $C_1$-$C_4$fluoroalkylphenyl, nitrophenyl or by cyanophenyl, or with $C_1$-$C_{12}$acyl-$X^1$ wherein $X^1$ is —Cl, —Br, $C_1$-$C_6$alkoxy or the radical of a secondary amine, or with $X^2C_nH_{2n}COOR^2$, $X^2$—$CR^3$=$CR^4R^5$ or a compound of formula IIIa

 (IIIa)

wherein $X^2$ is a leaving group, and c) isolating the compound of formula I or first hydrolysing the reaction mixture and then isolating the compound of formula I.

A preferred process in this connection is considered to be that for the preparation of compounds of formula I,

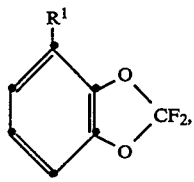

wherein $R^1$ is —CHO, —CN, —COOH, —COX, with X being Cl or Br, —COOR$^2$, with $R^2$ being a $C_1$-$C_{12}$alcohol moiety without the hydroxy group, —$C_nH_{2n}$COOR$^2$, with n being an integer from 1 to 4, linear or branched $C_1$-$C_{12}$hydroxyalkyl or $C_1$-$C_{12}$acyl each unsubstituted or substituted by —F, —CN, $C_1$-$C_6$alkoxy, phenyl, fluorophenyl, $C_1$-$C_4$alkoxyphenyl, $C_1$-$C_4$alkylthiophenyl, $C_1$-$C_4$alkylphenyl, $C_1$-$C_4$fluoroalkylphenyl, nitrophenyl or by cyanophenyl, or is a radical of formula II

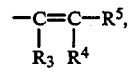

wherein $R^5$ is —CN, —CF$_3$, —COOR$^2$ or —CONR$_2^2$, $R^3$ and $R^4$ are a direct bond or each is H, or $R^3$ is H and $R^4$ independently has the meanings of $R^5$, or $R^3$ and $R^4$ together are —CH$_2$—NR$^6$—CH$_2$—, —CH$_2$—NR$^6$—CO— or —CO—NR$^6$—CO— wherein $R^6$ is the radical of a removable protecting group, or wherein $R^1$ is a radical of the formula III

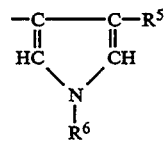

which process comprises
a) in an inert solvent, reacting 2,2-difluorobenzo-1,3-dioxole with an alkali metal or with an alkali metal compound with a strong anion base to give a compound of formula IV

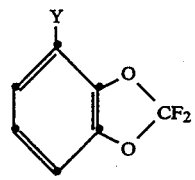

wherein Y is an alkali metal, and optionally then reacting with an anhydrous metal halide from the group MgZ$_2$, ZnZ$_2$, CdZ$_2$, CuZ, CuZ$_2$, PdZ$_2$, NiZ$_2$, AlZ$_3$, SiZ$_4$, SnZ$_2$, SnZ$_4$, TiZ$_4$, or ZrZ$_4$ to give a compound of formula IV wherein Y is —Cu, —MgZ, —ZnZ, —CdZ, —CuZ, —PdZ, —NiZ, —AlZ$_2$, —SiZ$_3$, —SnZ, —SnZ$_3$, —TiZ$_3$ or —ZrZ$_3$ and Z is —Cl, —Br or —I,
b) reacting the compound of formula IV with an electrophilic compound from the group X—CN, CO$_2$, COX$_2$ or XCOOR$^2$, with X being —Cl or —Br, or with a formylating reagent, a $C_2$-$C_{12}$haloalcohol which is unsubstituted or is substituted by —F, —CN, $C_1$-$C_6$alkoxy, phenyl, fluorophenyl, $C_1$-$C_4$alkoxyphenyl, $C_1$-$C_4$alkylthiophenyl, $C_1$-$C_4$alkylphenyl, $C_1$-$C_4$fluoroalkylphenyl, nitrophenyl or by cyanophenyl, CH$_2$O, a $C_1$-$C_{11}$alkyl-CHO which is unsubstituted or is substituted by —F, —CN, $C_1$-$C_6$alkoxy, phenyl, fluorophenyl, $C_1$-$C_4$alkoxyphenyl, $C_1$-$C_4$alkylthiophenyl, $C_1$-$C_4$alkylphenyl, $C_1$-$C_4$fluoroalkylphenyl, nitrophenyl or by cyanophenyl, an epoxide, a benzaldehyde which is unsubstituted or is substituted by —F, $C_1$-$C_4$alkoxy, $C_1$-$C_4$alkylthio, $C_1$-$C_4$alkyl, $C_1$-$C_4$fluoroalkyl, nitro or by cyano, or with $C_1$-$C_{12}$acyl-X$^1$ wherein X$^1$ is —Cl, —Br, $C_1$-$C_6$alkoxy or the radical of a secondary amine, or with X$^2C_nH_{2n}$COOR$^2$, X$^2$—CR$^3$=CR$^4$R$^5$ or a compound of formula IIIa

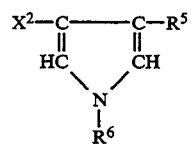

wherein X$^2$ is a leaving group, and
c) isolating the compound of formula I or first hydrolysing the reaction mixture and then isolating the compound of formula I.

Prominence is to be given in this connection to that variant for the preparation of compounds of formula I wherein $R^1$ is —CHO or a radical of formula II

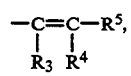

wherein $R^5$ is —CN, —COOR$^2$ or —CONH$_2$, each of $R^3$ and $R^4$ is H, or $R^3$ is H and $R^4$ independently has the meaning of $R^5$. The process wherein $R_1$ is —CHO is of specific interest. This process is preferably carried out with butyllithium as metallating agent, in the presence of a complex forming compound at from $-15°$ to $+10°$ C.

When $R^2$ is an alcohol moiety without a hydroxy group it can be, for example, linear or branched alkyl having preferably from 1 to 12, especially from 1 to 6, carbon atoms, or unsubstituted or $C_1$-$C_4$alkyl-substituted $C_5$- or $C_6$-cycloalkyl or $C_5$- or $C_6$-cycloalkyl-$C_mH_{2m}$- or phenyl-$C_mH_{2m}$ wherein m is 0 or an integer from 1 to 4, especially 0, 1 or 2. Examples are methyl, ethyl, the isomers of propyl, butyl, pentyl, hexyl, octyl, decyl, dodecyl, cyclopentyl, cyclohexyl, methylcyclopentyl or methylcyclohexyl, (methyl- or ethylcyclohexyl)methyl, benzyl, methyl- or ethyl-benzyl, phenylethyl or (methylphenyl)ethyl.

When $R^1$ is $C_nH_{2n}$COOR$^2$, n is an integer from 1 to 4, especially 1 or 2. The —$C_nH_{2n}$— group may be linear or branched. Examples of this group are methylene, ethylene, ethylidene, propylidene, 1,2- or 1,3-propylene, butylidene, 1,2-, 1,3- or 1,4-butylene.

When $R^1$ is unsubstituted or substituted hydroxyalkyl, it contains preferably from 1 to 6, especially from 1 to 4, carbon atoms. The hydroxy group may be bonded to a primary, secondary or tertiary carbon atom. Examples of hydroxyalkyl or hydroxymethyl, 1- or 2-hydroxyethyl, 1-, 2- or 3-hydroxyprop-1- or -2-yl, 1-, 2-, 3- or 4-hydroxybut-1- or -2-yl, hydroxypentyl, hydroxyhexyl, phenyl(hydroxymethyl), 1-phenyl-2-hydroxyethyl, fluorophenyl(hydroxymethyl), 1-methoxy-2-hydroxyeth-2-yl, 1,1,1-trifluoro-2-hydroxyethyl and cyanophenyl(hydroxymethyl).

When $R^1$ is unsubstituted or substituted acyl, it contains preferably from 1 to 6 and especially from 1 to 4 carbon atoms. The acyl radical may, for example, be one of formula $R^7$—CO— wherein $R^7$ is $C_1$-$C_{11}$alkyl, especially $C_1$-$C_6$alkyl, which is unsubstituted or is substituted by —F, —CN, $C_1$-$C_6$alkoxy, phenyl, fluorophenyl, $C_1$-$C_4$alkoxyphenyl, $C_1$-$C_4$alkylphenyl, $C_1$-$C_4$alkylthiophenyl, $C_1$-$C_4$fluoroalkylphenyl, nitrophenyl or by cyanophenyl, or may be phenyl which is unsubstituted or is substituted by —F, cyano, nitro, $C_1$-$C_4$alkyl, $C_1$-$C_4$alkoxy, $C_1$-$C_4$alkylthio or by $C_1$-$C_4$fluoroalkyl. Examples are formyl, acetyl, fluoroacetyl, trifluoroacetyl, chlorodifluoroacetyl, propionyl, butyryl, benzoyl, phenylacetyl, 3-phenylpropionyl or fluorobenzoyl.

As the radical of a secondary amine, $X^1$ contains preferably from 2 to 12, especially from 2 to 8, carbon atoms. The radical may correspond to the formula $R^8R^9N$— wherein $R^8$ is $C_1$-$C_6$alkyl or $C_1$-$C_6$alkoxy and $R^9$ is $C_1$-$C_6$alkyl, or $R^8$ is $C_1$-$C_4$alkoxy-$C_1$-$C_3$alkyl and $R^9$ is $C_1$-$C_6$alkyl or has the meaning of $R^8$, or $R^8$ and $R^9$ together are tetra- or penta- methylene or tetra- or penta-methylene interrupted by —O— or by a =N—$C_1$-$C_4$alkyl group. In a preferred embodiment, $X^1$ is

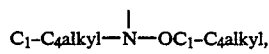

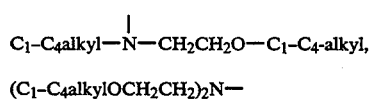

$(C_1$-$C_4$alkylOCH$_2$CH$_2)_2$N— or the radical of a 5- or 6-membered heterocyclic amine which may contain a further hetero atom from the group —O— and =N—$C_1$-$C_4$alkyl. Examples are dimethylamino, diethylamino, methoxymethylamino, ethoxymethylamino, methyl(methoxyethyl)amino, di(methoxymethyl)amino, pyrrolidino, piperidino, morpholino and N-methylpiperazino.

$R^5$ is preferably —CN, —CF$_3$, —COOR$^2$ or —CONH$_2$.

The removable protecting group $R^6$ is generally a known radical. $R^6$ may, for example, be $C_1$-$C_4$alkoxymethyl, or phenoxymethyl which is unsubstituted or substituted by $C_1$-$C_4$alkyl or $C_1$-$C_4$alkoxy. Suitable groups are also benzyl, diphenylmethyl and triphenylmethyl. In a preferred embodiment the protecting groups are trialkylsilyl groups having a total of from 1 to 18, preferably from 1 to 10, carbon atoms, $C_1$-$C_{12}$acyl, especially $C_1$-$C_6$acyl, groups or —COOR$^2$ groups in which $R^2$ has the meanings mentioned hereinbefore. The trialkylsilyl group may be, for example, trimethylsilyl, triethylsilyl, tri-n- or -iso-propylsilyl, tert.-butyldimethylsilyl or (1,1,2,2-tetramethylethyl)dimethylsilyl. Acyl groups have been mentioned hereinbefore for $R^1$. In the group —COOR$^2$, $R^2$ is preferably $C_1$-$C_6$alkyl. Examples of these groups are methoxycarbonyl, ethoxycarbonyl, propoxycarbonyl, butoxycarbonyl, pentyloxycarbonyl and hexyloxycarbonyl.

The leaving group $X^2$ is preferably a halide, especially —Cl or —Br, $C_1$-$C_6$alkoxy, for example methoxy, ethoxy or propoxy, $C_6$-$C_{10}$aryloxy, for example phenoxy or naphthoxy, $C_1$-$C_{12}$-secondary amino, especially $C_1$-$C_6$-secondary amino, for example dimethylamino, diethylamino, piperidino, $C_1$-$C_8$-acyloxy, especially $C_1$-$C_4$acyloxy, for example acetyloxy, or the radical of a sulfonic acid which may be an aliphatic sulfonic acid, for example methyl-, ethyl- or propyl-sulfonic acid, or an aromatic sulfonic acid, for example benzene- or p-toluene-sulfonic acid.

2,2-Difluorobenzo-1,3-dioxole is known and can be obtained, for example, by fluorination of 2,2-dichlorobenzo-1,3-dioxole.

Reaction step a) is carried out in an inert solvent, for example in a non-polar or polar aprotic solvent. Suitable solvents are aliphatic or aromatic hydrocarbons, ethers, tertiary amines, N-alkylated acid amides, lactams or cyclic ureas, sulfoxides, sulfones, nitriles, or mixtures thereof. Examples are pentane, isopentane, hexane, heptane, cyclohexane, methylcyclohexane, benzene, toluene, xylene, diethyl ether, dibutyl ether, tetrahydrofuran, dioxane, ethylene glycol dimethyl ether, triethylamine, N,N,N',N'-tetramethylethylenediamine, hexamethylphosphoric acid triamide, dimethylformamide, dimethylacetamide, N-methylpyrrolidone, ethylenedimethylurea, propylenedimethylurea, dimethyl sulfoxide, tetramethylenesulfone, acetonitrile. Solvents that may at the same time be reactants in process step b), such as, for example, carboxylic acid amides, are not added until process step b) and are then added in the form of an excess of those reactants.

The reaction temperature may preferably be from −150° to 150° C., especially from −30° to +10° C., in both process steps when the reaction is carried out with butyllithium as metalating agent.

If non-polar or weakly polar solvents are employed, it is advantageous for the reaction mixture to contain, in addition, a complexing agent, for example in an amount of from 0.01 mol. % up to 10-fold excess, based on the compound of formula IV. Such complexing agents may be, for example, tertiary amines or N-substituted acid amides, lactams or cyclic ureas, ethers or sulfoxides, such as those mentioned hereinbefore under solvents.

Of the process conditions, the use of complex-forming compound selected from a group consisting of tert.-amines, cyclic ureas, ethers and N-substituted acid amides is preferred. Of those, hexamethylphosphoric acid triamide, ethylene glycol dimethyl ether, 1,3-dimethyl-2-imidazolone, dimethylethyleneurea, dimethylpropyleneurea and N,N,N',N'-tetramethylethylenediamine are especially preferred.

Further suitable complexing agents are crown ethers, such as, for example, 15-crown-5, 18-crown-6, dibenzo-18-crown-6, dicyclohexyl-18-crown-6, dibenzo-24-crown-8 or dicyclohexyl-24-crown-8. Alkali metal halides, especially lithium, sodium and potassium halides, magnesium halide and copper halide are also suitable. Halide is preferably chloride, bromide and iodide.

Suitable alkali metals and alkaline earth metals, also in the alkali metal and alkaline earth metal compounds, for use in reaction step a) are, for example, Li, Na, K, Rb, Cs, Ca, Sr or Ba, with Li, Na and K being preferred. The strongly basic anions may be, for example, linear or branched $C_1$-$C_6$alkyl$^\ominus$, especially $C_1$-$C_4$alkyl$^\ominus$, $C_6$-$C_{14}$aryl$^\ominus$, HO$^\ominus$, H$_2$N$^\ominus$, H$^\ominus$, $C_1$-$C_6$alkoxy$^\ominus$, especially $C_1$-$C_4$alkoxy$^\ominus$, $C_1$-$C_6$alkyl-NH$^\ominus$, especially $C_1$-$C_4$alkyl-NH$^\ominus$, or di($C_1$-$C_6$alkyl)N$^\ominus$, especially di($C_1$-$C_4$alkyl)N$^\ominus$, or di($C_3$-$C_6$cycloalkyl)N$^\ominus$. In a preferred embodiment, the alkali metal is Li, Na or K and the alkali metal or alkaline earth metal compound is a Li-, Na-, K-, Ca-, Sr- or Ba-alkyl, -arylhydride, -amide or -alcoholate.

The metallation of 2,2-difluorobenzo-1,3-dioxole is effected in a manner known per se by reaction thereof with an alkali metal or with an alkali metal or alkaline earth metal compound in an inert solvent at preferably from −80° to 20° C. In this reaction, the alkali metal, for example in the form of a suspension, or the alkali metal or alkaline earth metal compound can be introduced into the reaction vessel first and the benzodioxole can be slowly added thereto. The procedure may also be reversed.

Reaction b) can be carried out directly after reaction step a). It is also possible, however, for the alkali metal or alkaline earth metal compound of formula IV to be reacted prior to reaction step b) with an anhydrous metal halide, for example $MgZ_2$, $ZnZ_2$, $CdZ_2$, $CuZ$, $CuZ_2$, $PdZ_2$, $NiZ_2$, $AlZ_3$, $SiZ_4$, $SnZ_2$, $SnZ_4$, $TiZ_4$, $BZ_3$ or $ZrZ_4$ wherein Z is Cl, Br or I, especially Cl or Br, to give a compound of formula IV wherein Y is —MgZ, —ZnZ, —CdZ, —CuZ, —PdZ, —NiZ, —$AlZ_2$, —$SiZ_3$, —SnZ, —$SnZ_3$, —$TiZ_3$, —$BZ_2$ or —$ZrZ_3$. Z is especially Cl or Br. In this reaction, the metal halide can be added in solid form or in the form of a suspension in an inert solvent. The reaction temperature is preferably from 0° to −80° C.

The electrophilic compounds used in reaction step b) are known or can be prepared by known processes. A few examples are cyanogen chloride or bromide, carbon dioxide, carboxylic acid dichloride or dibromide, methyl chlorocarbonate, ethyl bromocarbonate; formylating reagents preferably from the group $C_1$-$C_6$alkoxymethyleneanilines, formates having preferably from 1 to 6, especially from 1 to 4, carbon atoms in the alcohol moiety, for example methyl or ethyl formate, orthoformic acid esters having preferably from 1 to 6 carbon atoms in the alcohol moiety, N-disubstituted formamides having from 2 to 12, preferably from 2 to 6, carbon atoms and, optionally —O— or N—$C_1$-$C_4$alkyl groups in the amide radical, for example dimethyl-, diethyl-, methyl-methoxyformamide, formic acid morpholide or formic acid N-methylpiperazide; formaldehyde, acetaldehyde, benzaldehyde, acetyl chloride or bromide, propionyl chloride, methyl acetate, ethyl propionate, dimethylacetamide, N-methyl-N-methoxypropionic acid amide, ethyl benzoate, N,N-dimethylphenylacetic acid amide, ethyl chloroacetate or bromoacetate, 2-chloro- or 2-bromo-ethanol, 2-chloro- or 2-bromopropan-1-ol, 4-chlorobutan-1-ol, 3-chloro- or 3-bromo-propynoic acid nitrile, 1-chloro- or 1-bromo-3,3,3-trifluoropropyne, ethyl 3-chloropropynecarboxylate, ethoxyacetonitrile, 1-ethoxy-3,3,3-trifluoroprop-1-ene, ethylene oxide, propylene oxide, ethyl β-dimethylaminoacrylate, β-p-toluenesulfonyloxyacrylonitrile, N,N-dimethyl-β-chloroacrylic acid amide, β-ethoxy-acrylonitrile, β-p-toluenesulfonyloxy-α-cyanoacrylonitrile, ethyl N,N-dimethylaminomethylenecyanoacetate, α-trifluoromethyl-β-chloroacrylonitrile, ethyl ethoxymethylenecyanoacetate, ethyl p-toluenesulfonyloxymethylenecyanoacetate, Δ3-1-acetyl-3-cyano-4-chloropyrroline, Δ3-1-trimethylsilyl-3-cyano-4-tosyloxy-pyrrolin-2-one, 1-acetyl-3-cyano-4-chloropyrrole, trimethyl borate, triphenyl borate, trimethylchlorosilane, diphenylmethylchlorosilane, sulfur. Formylating reagents are described by Olah et al. in Chem. Rev. 1987, 87, page 671. Of this formylating agents, attention is drawn to dimethyl formamide.

It may be of advantage to carry out reaction b) in the presence of Pd, Rh or Ru compounds.

The reaction temperature in step b) may, for example, be from −80° C. to 100° C., preferably from −80° C. to 50° C. The electrophilic compound may be added in solid form or in the form of a solution, it being possible for the solvent to be the same as or different from that used in reaction step a).

The isolation of the compounds of formula I is carried out by methods that are known per se by distilling, crystallising or chromatographing the filtrate obtained after filtration of the reaction mixture. It is generally advantageous to hydrolyse the reaction mixture, for example with dilute mineral acids, such as, for example, hydrochloric acid or sulfuric acid. If the electrophilic compound is $CO_2$, an aldehyde, an epoxide or a carboxylic acid amide or ester, salts will initially be formed which make hydrolysis necessary in order to isolate the compounds of formula I. The hydrolysis conditions are so selected that the protecting group $R^6$ is not split off.

In a preferred embodiment of the process for preparing 2,2-difluoro-1,3-benzodioxol-4-yl-carbaldehyd a suspension of n-butyllithium is reacted with the equivalent amount of tetramethylethylenediamine at −15° to −10° C., and the resulting mixture is added to 2,2-difluoro-1,3-benzodioxole at a maximum molar ratio of n-butyllithium to 2,2-difluoro-1,3-benzodioxole of 0.99 to 1.02 in an inert solvent and the reaction mixture is reacted in succession by adding an equivalent amount of dimethyl formamide to the reaction mixture, by hydrolysing the reaction mixture, and the reaction product is isolated.

In another preferred embodiment of this process a suspension of n-butyllithium is added at −15° C. to −10° C. to a solution of 2,2-difluoro-1,3-benzodioxole and of the approximately equimolar amount of tetramethylethylenediamine at a maximum molar ratio of n-butyllithium to 2,2-difluoro-1,3-benzodioxole of 0.99 to 1.02, in an inert solvent and the reaction mixture is reacted in succession by adding an equivalent amount of dimethyl formamide to the reaction mixture, by hydrolysing the reaction mixture, and the reaction product is isolated.

The continuous variant of this process makes it possible to carry out the reaction under constant conditions and at relatively elevated temperature up to +10° C. The yield can increased up to 98% of theory by combining these specific measures. Accordingly, this procent variant, wherein n-butyllithium is continuously fed into a prepared solution of difluoro-1,3-benzodioxole and tetramethylethylenediamine at −5° to +10° C., and the reaction mixture is immediately and continuously reacted with dimethyl formamide and hydrolised, is of specific interest.

The present invention also relates to a process for the preparation of 3-(2,2-difluorobenzodioxol-4-yl)-4-cyanopyrrole of formula V

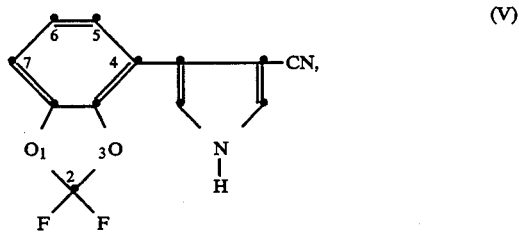

(V)

to the 4-metallo-2,2-difluorobenzodioxoles involved as intermediate of that process, and to a process for the preparation of those intermediates.

It is known from DE-PS 2,927,480 that N-acyl-3-phenyl-4-cyanopyrroles have a fungicidal activity.

A process for the preparation of 3-phenyl-4-cyanopyrroles starting from an α-cyanocinnamic acid (or from a suitable ester of such an acid) by reaction with a substituted methyl isocyanide has been described in DE-OS 3,601,285.

The disadvantage of that process is that the benzaldehydes, which, as the starting materials, form the basis of the α-cyanocinnamic acids, can be obtained only with difficulty in the case of certain substitutions in the nucleus. In such cases, a process based on that reaction sequence proves to be very difficult to carry out and uneconomical.

The aim of the present invention is to provide a process for the preparation of 3-(2,2-difluorobenzodioxol-4-yl)-4-cyanopyrrole which process is improved from the technical and economic point of view and can be applied generally.

Surprisingly, it has now been found that 3-(2,2-difluorobenzodioxol-4-yl)-4-cyanopyrrole of formula V

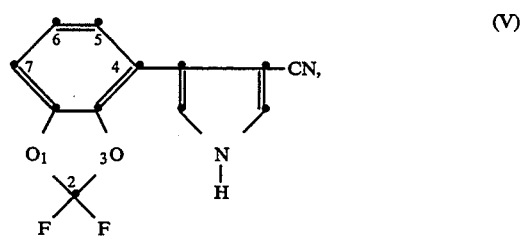

(V)

can be very readily prepared in a one-pot process when a 4-metallo-2,2-difluorobenzodioxole of formula VII, wherein Me is a metal, m is the valency of that metal and A is an anionic radical which can also be a $C_1$–$C_{14}$ organic basic radical, is reacted in a solvent phase, in the presence or absence of complex-forming compound, first with an unsaturated nitrile of formula VIII

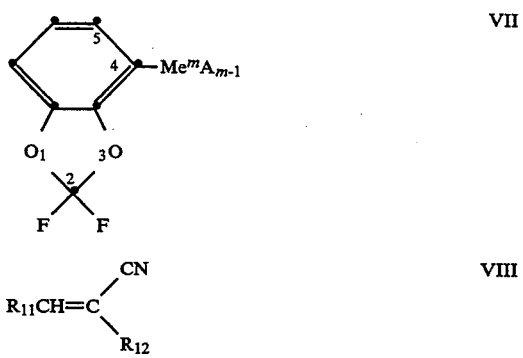

VII

VIII wherein $R_{11}$ is halogen, $C_1$–$C_4$alkoxy, $C_6$–$C_{10}$aryloxy, di-$C_1$–$C_4$alkylamino, $C_1$–$C_4$alkylsulfonyloxy, $C_6$–$C_{10}$arylsulfonyloxy or $C_1$–$C_4$alkylcarbonyloxy (=acyloxy) and $R_{12}$ is a $C_1$–$C_4$alkoxycarbonyl radical, and then with an isocyanide of formula IX

$R_{13}$—$SO_2CH_2NC$,   (IX)

wherein $R_{13}$ is an open-chain or cyclic, unsubstituted or substituted $C_1$–$C_{10}$hydrocarbon.

It has also been found and is likewise a subject of the present invention that the compounds of formula VII can be prepared very readily and regioselectively by reacting 2,2-difluorobenzodioxole of formula VI in a suitable solvent phase, in the presence or absence of a complex-forming compound, with a metal or a metal compound, metallation not occurring to any appreciable extent in any position other than the 4-position.

In these formulae, Me, A and m are as defined above, at least one A being an organic basic radical. If a metal is used, m=0 and A does not apply.

The nature of the metal Me used and also of the metal compound $Me^mA_m$ used is not in principle subject to any restriction but metals of the alkali or alkaline earth groups are preferred, especially Li, Na, K, Cs, Ca and Mg and their compounds with a $C_1$–$C_{10}$hydrocarbon radical, or with amines e.g. with 2,2,6,6-tetramethyl piperidine.

The reaction is carried out in a temperature range of from −70° to +150° C., preferably at from −25° to +80° C.

Suitable solvents are, for example, hydrocarbons (such as petroleum ether, toluene, hexane, heptane, etc.) and ethers (such as diethyl ether, dioxane, tetrahydrofuran) in addition to those specified hereinafter. If nonpolar or weakly polar solvents are used in the metallation, then the use of complexing agents is necessary or at least advantageous if a high regioselectivity is to be obtained and ensured.

Of the process conditions, the use of a complex-forming compound selected from a group consisting of tert.-amines, cyclic ureas, ethers and N-substituted acid amides is preferred. Of those, hexamethylphosphoric acid triamide, ethylene glycol dimethyl ether, 1,3-dimethyl-2-imidazolone, dimethylethyleneurea, dimethylpropyleneurea and N,N,N',N'-tetramethylethylenediamine are especially preferred.

The present invention relates also to the compounds of formula VII which can be prepared by that process.

Compounds of formula VII can also be obtained by trans-metallation of a compound of formula VIIa

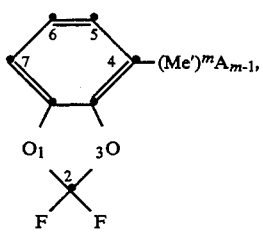

(VIIa)

with a compound of formula $Me'^m A_{m}$, Me' being a metal other than Me. The meaning of the metal Me' and its compounds is limited essentially to metals of the alkali and alkaline earth group. Preferred are Li, Na, K, Cs and Mg, lithium being especially preferred. The present invention relates also to that transmetallation. Alkali metal and alkaline earth metal derivatives of 2,2-difluorobenzodioxole can generally be obtained by direct metallation, while metals from the other groups are advantageously obtained from the former group by transmetallation. The present invention relates also to the 4-metallo-2,2-difluorobenzodioxole derivatives of formula VII obtainable by transmetallation or direct metallation, especially to those in which the metal is an alkali metal or an alkaline earth metal or is zinc, cadmium, copper, palladium, nickel, aluminium, silicon, tin, titanium or zirconium.

In such a transmetallation operation, for example 2,2-difluorobenzodioxole-lithium can be converted with magnesium bromide or with zinc chloride into 2,2-difluorobenzodioxole-magnesium bromide or 2,2-difluorobenzodioxole-zinc chloride, respectively.

Surprisingly, it has now been found that, starting from 2,2-difluorobenzodioxole of formula VI, the complete process for the preparation of the compounds of formula V can be effected in a one-pot process via the stage of the compounds of formula VII despite the fact that the reactants are completely different and are added gradually and possibly under changing conditions, likewise without isolation of further products formed intermediately.

The present invention accordingly relates also to a process for the preparation of 3-(2,2-difluorobenzodioxol-4-yl)-4-cyanopyrrole, wherein the 2,2-difluorobenzodioxole of formula VI is converted in a solvent phase, in the presence or absence of a complex-forming compound, with an organometal compound or with a metal into a 4-metallo-2,2-difluorobenzodioxole of formula VII which is reacted, without being isolated, first with an unsaturated nitrile of formula VIII and then with an isocyanide of formula IX.

Metal compounds of formula VII are therefore the direct intermediates for compounds of formula V and are either introduced as such into the preparation process or are formed in the first step thereof.

Using the process according to the invention, 3-(2,2-difluorobenzodioxol-4-yl)-4-cyanopyrrole can be prepared in a high yield.

The $C_1$–$C_4$alkyl representing the individual radicals, $R_{11}$ and $R_{12}$ in formula VIII as part of other radicals may be branched or straight-chained and is methyl, ethyl, propyl, isopropyl, butyl, sec.-butyl, isobutyl or tert.-butyl.

$R_{11}$ as a $C_6$–$C_{10}$aryloxy or a $C_6$–$C_{10}$arylsulfonyloxy radical may be phenoxy, $C_1$–$C_4$alkylphenoxy, α- or β-naphtyloxy, further phenylsulfonyloxy, $C_1$–$C_4$alkylsulfonyloxy or α- or β-naphthylsulfonyloxy.

There may be mentioned as examples of the $C_1$–$C_1$₀hydrocarbon radical mentioned under $R_{13}$ in formula IX, without these constituting a limitation, methyl, ethyl, isopropyl, heptyl, octyl, cyclopentyl, cyclohexyl, decyl, methylcyclohexyl, phenyl, p-tolyl, 1-naphthyl and 2-naphthyl.

In the metallation reagents $Me^m A_m$ for the 2,2-difluorobenzodioxole, as mentioned, at least one A is a strongly basic anion which may be $C_1$–$C_{10}$alkyl⁻, preferably $C_1$–$C_4$alkyl⁻, $C_6$–$C_{14}$aryl⁻, $C_1$–$C_{10}$alkoxy⁻, preferably $C_1$–$C_4$alkoxy⁻, $NH_2$⁻, $C_1$–$C_{10}$hydrocarbylNH⁻ or di($C_1$–$C_{10}$hydrocarbyl)N⁻, di($C_5$–$C_{10}$cycloalkyl)N⁻ or also H⁻.

Of these anions, alkyl⁻, aryl⁻ (such as phenyl⁻) di-($C_1$–$C_4$alkyl)N⁻, ($C_1$–$C_4$alkyl)($C_5$–$C_6$cycloalkyl)N⁻ and di-($C_5$–$C_6$cycloalkyl)N⁻ are preferred. For transmetallation it is also possible to use metal compounds having anions such as halide, nitrate, sulfate, phosphate, acetate, formate, etc..

The following solvents are especially suitable for the preparation of the compounds of formula V in stepwise processes or in a one-pot process:

Aliphatic or aromatic hydrocarbons, ethers, tertiary amines, N-alkylated acid amides, lactams or cyclic ureas, sulfoxides, sulfones, nitriles, ketones, alcohols or mixtures thereof. Examples are pentane, isopentane, hexane, heptane, cyclohexane, methylcyclohexane, benzene, toluene, xylene, diethyl ether, dibutyl ether, tetrahydrofuran, dioxane, ethylene glycol dimethyl ether, triethylamine, N,N,N', N'-tetramethylethylenediamine, hexamethylphosphoric acid triamide, dimethylformamide, dimethylacetamide, N-methylpyrrolidone, ethylenedimethylurea, propylenedimethylurea, dimethyl sulfoxide, tetramethylenesulfone, acetonitrile, acetone, methyl ethyl ketone, methyl isobutyl ketone, cyclohexanone, methanol, ethanol, isopropanol and tert.-butanol.

When non-polar solvents are used, in order to ensure that the reaction proceeds smoothly it is almost always necessary to add a complexing agent, and when weakly polar solvents are used such action is at least advantageous. The complexing agent is added in an amount of from 0.01 mol. % to a tenfold excess, based on the compound of formula VI. Tertiary amines, N-substituted acid amides, lactams, cyclic ureas, alcoholates, sulfoxides or ethers, some of which have already been mentioned among the above solvents or earlier among the preferred complexing agents, are generally suitable.

Included among the ethers in the broader sense are also crown ethers, for example 15-crown-5; 18-crown-6; dibenzo-18-crown-6; dicyclohexyl-18-crown-6; dibenzo-24-crown-8; and dicyclohexyl-24-crown-8.

The processes according to the invention preferably take place under an inert gas in the presence of a complex-forming compound (=complexing agent) and in a solvent or a solvent mixture.

The preferred first step in each of the above-mentioned processes for the preparation of the compounds of formula VII, VIIa or V is the metallation of the 2,2-difluorobenzodioxole of formula VI with lithium or, preferably, an organolithium compound. Accordingly, of the compounds of formula VII, 2,2-difluorobenzodioxol-4-yl-lithium is especially preferred as intermediate.

One of the preferred forms of the complete process for the preparation of 3-(2,2-difluorobenzodioxol-4-yl)-4-cyanopyrrole is that wherein the 2,2-difluoro-1,3-benzodioxole dissolved in a hydrocarbon is added at from −25° to −5° C. to a mixture of approximately equimolar amounts of tetramethylethylenediamine and n-butyllithium, and then an equimolar amount of ethoxymethylenecyanoacetic acid ethyl ester and subsequently an equimolar amount of p-toluenesulfonylmethyl isocyanide are added to the reaction mixture at from −25° to +25° C. Tetrahydrofuran is advantageously used as a further solvent. Methanol may be mentioned as the preferred solvent for the last reactant.

One of the especially preferred forms of the complete process for the preparation of 3-(2,2-difluorobenzodioxol-4-yl)-4-cyanopyrrole is that wherein n-butyllithium is added at from −25° to −5° C. to a mixture, dissolved in a hydrocarbon, of approximately equimolar amounts of 2,2-difluorobenzodioxole and tetramethylethylenediamine, and then an equimolar amount of ethoxymethylenecyanoacetic acid ethyl ester and subsequently an equimolar amount of p-toluenesulfonylmethyl isocyanide are added to the reaction mixture at from −25° to +25° C.

The organometal compounds of formula VII, both in solution and in suspension, are stable for a time at low temperatures in the form of their corresponding complexes. It is known that, for example, organolithium compounds are often in the form of dimers. In addition, solvents or complexing agents that have free electron pairs, for example ethers or tert.-amines, are coordinatively bonded to the metal.

In the preparation according to the invention of the compounds of formula VII from the compound of formula VI, organometal compounds are to be given prominence as reactants. Of the organometal compounds, the organolithium compounds, especially methyllithium, n-butyllithium, sec.-butyllithium, tert.-butyllithium, phenyllithium, lithium diisopropylamide and lithium dicyclohexylamide, are particularly preferred.

The metal compounds used for the preparation of the compounds of formula VII, and the compounds of formulae VI, VIII and IX are known products which are commercially available or can be prepared by conventional methods.

The invention further relates to compounds of formula Ia

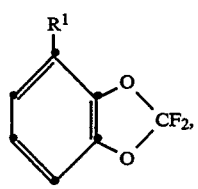
(Ia)

wherein $R^1$ is —OH, —SH, —CN, —COOH, —B(OH)$_2$, —COX, with X being Cl or Br, or is —COOR$^2$, —SiR$_3^2$ or —B(OR$^2$)$_2$, with R$^2$ being a C$_1$–C$_{12}$alcohol moiety without the hydroxy group, wherein R$^1$ is further —C$_n$H$_{2n}$COOR$^2$, with n being an integer from 1 to 4, or linear or branched C$_1$–C$_{12}$hydroxyalkyl which is unsubstituted or is substituted by —F, —CN, C$_1$–C$_6$alkoxy, phenyl, fluorophenyl, C$_1$–C$_4$alkoxyphenyl, C$_1$–C$_4$alkylthiophenyl, C$_1$–C$_4$alkylphenyl, C$_1$–C$_4$fluoroalkylphenyl, nitrophenyl or by cyanophenyl, or wherein R$^1$ is a benzyl alcohol or C$_1$–C$_{12}$acyl moiety, each unsubstituted or substituted by F, C$_1$–C$_4$alkoxy, C$_1$–C$_4$alkylthio, C$_1$–C$_4$alkyl, C$_1$–C$_4$fluoroalkyl, nitro or by cyano, or wherein R$^1$ is a radical of formula II

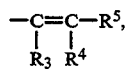
(II)

wherein $R^5$ is —CN, —CF$_3$, —COOR$^2$, —CONH$_2$, —CO—NHR$^2$ or —CONR$_2^2$, R$^3$ and R$^4$ are a direct bond or each is H, or R$^3$ is H and R$^4$ independently has the meanings of R$^5$, or R$^3$ and R$^4$ together are —CH$_2$—NR$^6$—CH$_2$—, —CH$_2$—NR$^6$—CO— or —CO—NR$^6$—CO— wherein R$^6$ is the radical of a removable protecting group, or wherein further R$^1$ is a radical of formula III

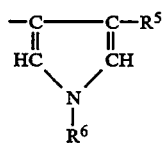
(III)

with the proviso that R$^5$ in formula III is not —CN. The preferred meanings indicated hereinbefore for R$^1$ to R$^6$, X$^1$ and X$^2$ also apply here.

Among these compounds, there are preferred those in which R$^1$ is —CN, —COOH, —B(OH)$_2$, —COX, with X being Cl or Br, or is —COOR$^2$ or —B(OR$^2$)$_2$, with R$^2$ being a C$_1$–C$_{12}$alcohol moiety without the hydroxy group, wherein R$^1$ is further —C$_n$H$_{2n}$COOR$^2$, with n being an integer from 1 to 4, or linear or branched C$_1$–C$_{12}$hydroxyalkyl or C$_1$–C$_{12}$acyl each unsubstituted or substituted by —F, —CN, C$_1$–C$_6$alkoxy, phenyl, fluorophenyl, C$_1$–C$_4$alkoxyphenyl, C$_1$–C$_4$alkylthiophenyl, C$_1$–C$_4$alkylphenyl, C$_1$–C$_4$fluoroalkylphenyl, nitrophenyl or by cyanophenyl, or wherein R$^1$ is a radical of formula II

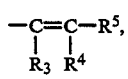
(II)

wherein $R^5$ is —CN, —CF$_3$, —COOR$^2$, —CONH$_2$, —CONHR$^2$ or —CONR$_2^2$, R$^3$ and R$^4$ are a direct bond or each is H, or R$^3$ is H and R$^4$ independently has the meanings of R$^5$, or R$^3$ and R$^4$ together are —CH$_2$—NR$^6$—CH$_2$—, —CH$_2$—NR$^6$—CO— or —CO—NR$^6$—CO— wherein R$^6$ is the radical of a removable protecting group, or wherein further R$^1$ is a radical of formula III

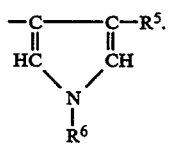
(III)

Preferred compounds of formula Ia are those in which R$^1$ is —CN, —COOH, —COOR$^2$, and R$^2$ is an alcohol moiety without a hydroxy group, or R$^1$ is —C$_n$H$_{2n}$COOR$^2$, with n being an integer from 1 to 4, or is a radical of formula II wherein each of R$^3$ and R$^4$ is H and R$^5$ is —CN, —CF$_3$, —CONR$_2^2$ or —COOR$^2$, or wherein R$^5$ is —CN, —CF$_3$, —COOR$^2$ or —CONR$_2^2$, R$^3$ and R$^4$ are a direct bond, or R$^3$ is H and R$^4$ independently has the meanings of R$^5$, or R$^3$ and R$^4$ together are —CH$_2$—NR$^6$—CH$_2$—, —CH$_2$—NR$^6$—CO— or —CO—NR$^6$—CO— wherein R$^6$ is the radical of a removable protecting group, or wherein $R^1$ is a radical of formula III, with the proviso that $R^5$ in formula III is not —CN. The preferred meanings indicated hereinbefore for $R^1$ to $R^6$, $X^1$ and $X^2$ also apply here.

Another preferred embodiment is that in which, in formula Ia, $R^1$ is or —COOR$^2$ or is a radical of formula II wherein $R^3$ and $R^4$ are a bond and $R^5$ is —CN, or $R^3$ is H, $R^4$ independently has the meanings of $R^5$ and $R^5$ is —CN, —COOR$^2$ or —CONR$_2^2$, or $R^3$ and $R^4$ together are —CH$_2$—NR$^6$—CH$_2$—, —CO—NR$^6$—CO— or —CH$_2$—NR$^6$—CO— and $R^5$ is —CN. $R^2$ is preferably a C$_1$-C$_6$alkyl radical. The protecting group $R^6$ is preferably a trialkylsilyl protecting group having a total of from 1 to 18 carbon atoms, a C$_1$-C$_{12}$acyl group or a —COOR$^2$ group.

Using the process of the invention, the compounds of formula I are obtained in high yield and purity whilst, in particular, position isomers are not formed or are formed only to an insignificant extent.

The compounds of formulae I and Ia are suitable for the preparation of insecticides and microbicides. The carboxylic acids and carboxylic acid derivatives, aldehydes and ketones can be reduced by customary methods of reduction to the corresponding alcohols. From the alcohols it is possible to prepare with pyrethroid or pyrethroid-like carboxylic acids insecticidal esters, such as those described in DE-OS 2 819 788 (Example 1).

Compounds of formula I are furthermore used as intermediates for valuable herbicides of the sulfonylurea class, such as, for example, those described in European Application Publication No. 99 339.

Compounds in which $R^1$ is —CN, —COOH, COX and COOR$^2$ can be converted by customary methods into the aldehyde group. From the aldehydes of formula I it is possible to prepare by the process described in EP-A-0 206 999 (Example 1) the microbicidal 3-cyanopyrroles described therein.

In compounds having radicals of formulae II and III, the —CF$_3$— group can be converted by the process described in U.S. Pat. No. 4,705,801 into the nitrile group. The conversion of ester and amide groups into nitrile groups is known, as is the hydrogenation of acetylenes to ethylenes. By using the known methods, it is possible to obtain compounds of formula I in which the group $R^1$ is —CH═CR$^4$R$^5$, wherein $R^4$ is H, —CN or —COOR$^2$ and $R^5$ is —CN or —COOR$^2$. These compounds are intermediates for the microbicides whose preparation using these intermediates is described in EP-A-0 206 999. The mentioned methods for conversion into the nitrile group and the dehydrogenation of compounds of formula I wherein $R^3$ and $R^4$ together are —CH$_2$—NR$^6$—CH$_2$— or —CH$_2$—NR$^6$—CO— also result in the microbicidal 3-cyanopyrroles mentioned. Compounds having the radical of formula III are themselves these 3-cyanopyrroles ($R^5$ is —CN) or can be converted into them, as mentioned, by known methods ($R^5$ is —CF$_3$, —COOR$^2$ or —CONR$_2^2$). Methods of removing the protecting group $R^6$ are widely described in the literature.

The following Examples illustrate the invention in detail.

EXAMPLE 1

Preparation of 4-(trifluoroacetyl)-2,2-difluoro-1,3-benzodioxole

In a 250 ml 3-necked flask under argon, 7.9 g (50 mmol) of 2,2-difluoro-1,3-benzodioxole are dissolved in a mixture of 30 ml of tetrahydrofuran and 30 ml of diethyl ether and, at —70° C., 40 ml (55 mmol) of tert.-butyllithium (1.39M in pentane) are added dropwise thereto over a period of 20 minutes. When the dropwise addition is complete, a yellow suspension is maintained at —70° C. for 40 minutes. There is then added dropwise at that temperature, over a period of 10 minutes, a solution of 9.8 g (50 mmol) of α,α,α-trifluoroacetyl-N-methylpiperazide in 20 ml of diethyl ether. The turbid solution is then allowed to warm up to 0° C. and is hydrolysed with 30 ml of 2N hydrochloric acid. The aqueous phase is separated off and extracted twice with 60 ml of diethyl ether each time. The organic solutions are washed once with 50 ml of 2N HCl and once with 50 ml of H$_2$O, dried over MgSO$_4$ and concentrated in a vacuum rotary evaporator. Upon distillation of the residue, 9.1 g (72%) of the product distil over in the form of a colourless liquid at boiling point (b.p.) 108°-110° C./40 mbar.

$^1$H-NMR (CDCl$_3$; 300 MHz): 7.62 (d×d; J7.9; 1.5; 1H); 7.29 (d×d; J 7.9; 1.5; 1H); 7.16 (t; J 7.9; 1H).

EXAMPLE 2

Preparation of 2,2-difluoro-1,3-benzodioxol-4-yl-carbaldehyde a) Under nitrogen, 69 ml (110 mmol) of n-butyllithium (1.60M in hexane) are introduced into a 500 ml 3-necked flask and, while cooling with ice/sodium chloride, a solution of 13 g (110 mmol) of N,N,N',N'-tetramethylenediamine (TMEDA) in 30 ml of hexane is added thereto over a period of 15 minutes. To the clear, pale yellow solution, 15.8 g (100 mmol) of 2,2-difluoro-1,3-benzodioxole dissolved in 120 ml of hexane are added dropwise, at —10° C., over a period of 30 minutes, during which 2,2-difluoro-1,3-benzodioxol-4-yllithium gradually separates in the form of a voluminous precipitate. After stirring vigorously at —10° C. for 30 minutes, 20 ml (260 mmol) of dimethylformamide (DMF) are added to the white suspension. The oily reaction mixture is stirred at —10° C. for 15 minutes and is then hydrolysed with 50 ml of 10% hydrochloric acid. The aqueous phase is separated off and extracted twice with 100 ml of diethyl ether each time. The organic solutions are washed three times with 40 ml of 1N HCl each time, dried over MgSO$_4$ and concentrated in a vacuum rotary evaporator at 50° C./200 mbar. Distillation yields 16.8 g (90% of theory) of colourless product of boiling point (b.p.) 75°-77° C./10 Torr.

b) The procedure of Example 3 is followed except that dimethylformamide is used instead of N-methyl-N-methoxy-acetamide. 2,2-Difluoro-1,3-benzodioxole-4-carbaldehyde is obtained in a yield of 73%.

c) 94.0 g (272 mmol) of n-butyllithium (18.5% in toluene) are added dropwise under a nitrogen atmosphere, at from —15° to —10° C., over a period of 1.5 hours, to 29.5 g (254 mmol) of N,N,N',N'-tetramethylethylenediamine and 40.0 g (253 mmol) of 2,2-difluoro-1,3-benzodioxole in 35 ml of toluene, an orange suspension being formed. 19.7 g (270 mmol) of DMF are then metered in at from —15° to —10° C. over a period of ½ hour. The pale yellow suspension is poured at +10° C. onto 346 g (1.105 mol) of 11.6% aqueous hydrochloric acid and the whole is stirred for ½ hour to complete the reaction. The aqueous phase is separated off and the organic phase is concentrated by evaporation in a vacuum rotary evaporator at 50° C./200 mbar under nitrogen to yield the desired product.

d) 39.3 g (339 mmol) of N,N,N',N'-tetramethylethylenediamine are added dropwise at from −15° to −10° C. under a nitrogen atmosphere to 137.8 g (409 mmol) of n-butyllithium solution (19.0% in toluene). The resulting reaction mixture is metered into a solution of 53.3 g (337 mmol) of 2,2-difluoro-1,3-benzodioxole in 46 ml of toluene over a period of 3½ hours at from −15° to −10° C. under a nitrogen atmosphere. 30 g (410 mmol) of N,N-dimethylformamide are then added over a period of ½ hour at from −15° to −10° C. The resulting solution is poured onto 461.1 g (1.472 mol) of 11.6% aqueous hydrochloric acid and the whole is stirred for ½ hour to complete the reaction. The aqueous phase is separated off and the organic phase is concentrated by evaporation in a vacuum rotary evaporator at 50° C./200 mbar under nitrogen to yield the desired aldehyde.

$^1$H-NMR (CDCl$_3$; 300 MHz): 10.20 (s; 1H); 7.58 (d×d; J 7.9; 1.5; 1H); 7.34 (d×d; J 7.9; 1.5; 1H); 7.23 (t; J 7.9; 1H).

e) The amounts of components according to Example c) are continuously reacted at a temperature of −5° C. to +10° C. The reaction is carried out in a 100 ml stirred double jacketed reaction tube. The n-butyllithium is continuously fed into a prepared solution of difluoro-1,3-benzodioxole and tetramethylethylenediamine at −5° to +10° C., and the reaction mixture is immediately and continuously reacted with dimethyl formamide and hydrolised. The yield is 98% of theory.

EXAMPLE 3

Preparation of 4-acetyl-2,2-difluoro-1,3-benzodioxole 6.2 g (55 mmol) of potassium tert.-butoxide dissolved in 40 ml of tetrahydrofuran (THF) are added dropwise at −30° C. under argon, over a period of 20 minutes, to a solution of 8.0 g (50 mmol) of 2,2-difluoro-1,3-benzodioxole in 10 ml of THF in a 250 ml 3-necked flask. The mixture is then cooled to −90° C. (methanol/liquid nitrogen), and 35 ml (55 mmol) of n-butyllithium (1.58M in hexane) are added thereto over a period of 30 minutes. The deep red solution of 2,2-difluoro-1,3-benzodioxol-4-yl-potassium is maintained at −78° C. for 20 minutes. Then, 5.2 g (50 mmol) of N-methyl-N-methoxy-acetamide in 20 ml of THF are added thereto over a period of 15 minutes at −78° C. When the dropwise addition is complete, the beige reaction mixture is allowed to warm up to −10° C. and is then hydrolysed with 40 ml of 10% hydrochloric acid. The hydrolysed mixture is extracted three times with 70 ml of diethyl ether each time. The organic solutions are washed three times with 30 ml of 1N HCl each time, dried over Na$_2$SO$_4$ and concentrated in a vacuum rotary evaporator. Upon distillation of the residue, 7.1 g (79%) of the product distil over in the form of a colourless oil at boiling point (b.p.) 114°–116° C./30 mbar.

$^1$H-NMR (CDCl$_3$; 300 MHz): 7.65 (d×d; J 7.9; 1.5; 1H); 7.27 (d×d; J 7.9; 1.5; 1H); 7.18 (t; J 7.9; 1H); 2.68 (s; 3H).

EXAMPLE 4

Preparation of 2,2-dimethyl-1-(2,2-difluoro-1,3-benzodioxol-4-yl)-propan-1-ol a) 23.7 ml (33 mmol) of tert.-butyllithium (1.4M in pentane) are added dropwise at −60° C. under argon, over a period of 20 minutes, to a solution of 4.75 g (30 mmol) of 2,2-difluoro-1,3-benzodioxole in 20 ml of tetrahydrofuran (THF) and 15 ml of diethyl ether in a 250 ml 3-necked flask.

The yellow, turbid solution is subsequently maintained at −65° C. for 30 minutes and then a fine suspension of 6.45 g (35 mmol) of anhydrous magnesium bromide in 35 ml of THF (prepared by 1,2-dibromethane and magnesium in THF) is added thereto over a period of 10 minutes. The greenish-blue solution is allowed to warm up to 0° C. and then 2.6 g (30 mmol) of pivalaldehyde dissolved in 10 ml of THF are added dropwise thereto. After stirring for 30 minutes at 25° C., the colourless reaction mixture is hydrolysed with 30 ml of 10% hydrochloric acid. The aqueous phase is separated off and extracted twice with 50 ml of diethyl ether each time. The organic solutions are washed once with 30 ml of 2N HCl and once with 30 ml of H$_2$O, dried over MgSO$_4$ and concentrated in a vacuum rotary evaporator. The crystalline yellow residue is recrystallised from hexane to yield 5.1 g (70%) of colourless platelets of melting point (m.p.) 68°–69° C.

b) The procedure of Example 1 is followed except that pivalaldehyde is used instead of trifluoroacetyl-N-methylpiperazide. 2,2-Dimethyl-1-(2,2-difluoro-1,3-benzodioxol-4-yl)-propan-1-ol is obtained in a yield of 81%.

$^1$H-NMR (CDCl$_3$; 300 MHz); 7.13 (d×d×d; J 8.0; 1.5; 0.5; 1H); 7.07 (t; J 8.0; 1H); 6.97 (d×d; J 8.0; 1.5; 1H); 4.63 (s; 1H); 2.05 (bs; OH), 0.95 (s; 9H).

EXAMPLE 5

Preparation of (E)-2-cyano-3-(2,2-difluoro-1,3-benzodioxol-4-yl)-2-propenoic acid ethyl ester a) 7.9 g (50 mmol) of 2,2-difluoro-1,3-benzodioxole are metallated according to Example 2 at −15° C. with 35 ml (55 mmol) of n-butyllithium (1.60M in hexane) and 6.5 g (55 mmol) of TMEDA in 60 ml of hexane. To the 2,2-difluoro-1,3-benzodioxol-4-yllithium which precipitates there is added at −20° C., over a period of 30 minutes, a solution of 9.3 g (55 mmol) of ethoxymethylenecyanoacetic acid ethyl ester in 30 ml of tetrahydrofuran, an orange-red turbid solution being formed during the reaction, which is exothermic. After stirring for 20 minutes at −15° C., the solution is hydrolysed with 50 ml of 2N hydrochloric acid. The aqueous phase is extracted twice with 80 ml of diethyl ether each time. The organic solutions are washed twice with 50 ml of water each time, dried over MgSO$_4$ and concentrated to dryness by evaporation in a vacuum rotary evaporator. The residue is crystallised from ethanol/water 4:1, affording 10.1 g (72%) of colourless platelets of m.p. 87°–88° C.

b) 40.0 g (253 mmol) of 2,2-difluoro-1,3-benzodioxole in 29.5 g (254 mmol) of TMEDA and 35 ml of toluene are metallated analogously to Example 2c) at from −15° to −10° C. with 106.2 g (307 mmol) of n-butyllithium solution (18.5% in toluene). 52.1 g (308 mmol) of ethoxymethylenecyanoacetic acid ethyl ester in 115 ml of toluene are added to the reaction mixture at from −15° to −10° C. over a period of 2 hours. The resulting suspension is poured, after 20 minutes at +10° C., into 350 ml of water, the aqueous phase is separated off and the organic phase is concentrated by evaporation in a vacuum rotary evaporator to yield the desired product.

c) 53.3 g (337 mmol) of 2,2-difluoro-1,3-benzodioxole in 46 ml of toluene are metalated according to Example 2d), at from −15° to −10° C., with 137.8 g (409 mmol)

of n-butyllithium solution (19.0% in toluene) in the presence of 39.3 g (339 mmol) of TMEDA. 69.1 g (409 mmol) of ethoxymethylenecyanoacetic acid methyl ester in 150 ml of toluene are metered in at from −15° to −10° C. over a period of 2½ hours. The reaction mixture is added at +10° C. to 450 ml of water, the phases are separated and the organic phase is concentrated by evaporation in a vacuum rotary evaporator to yield the title compound.

$^1$H-NMR (CDCl$_3$; 300 MHz); 8.35 (s; 1H); 8.10 (m; X of ABX; 1H); 7.25 (m; AB of ABX; 2H); 4.42 (q; J 7.0; 2H); 1.42 (t; J; 7.0; 3H).

EXAMPLE 6

The procedure of Example 4 is followed except that β-p-toluenesulfonyloxyacrylonitrile is used instead of pivalaldehyde. β-(2,2-Difluoro-1,3-benzodioxol-4-yl)acrylonitrile is obtained in a yield of 52%.

EXAMPLE 7

The procedure of Example 1 is followed except that CO$_2$ is passed in instead of adding trifluoroacetyl-N-methylpiperazide. 2,2-Difluoro-1,3-benzodioxol-4-carboxylic acid is obtained in a yield of 61%.

EXAMPLE 8

Preparation of 4-hydroxy-2,2-difluoro-1,3-benzodioxole 15.8 g (100 mmol) of 2,2-difluoro-1,3-benzodioxole are metallated according to Example 2, at −20° C., with 70 ml (110 mmol) of n-butyllithium (1.58M in hexane) and 12.8 g (110 mmol) of TMEDA in 120 ml of hexane. To the white suspension there is added dropwise at −100° C., over a period of 5 minutes, a solution of 10.4 g (100 mmol) of trimethyl borate in 50 ml of diethyl ether. When the reaction mixture has warmed up and has been stirred for 30 minutes at room temperature, there are added to the precipitated dimethoxy-(2,2-difluoro-1,3-benzodioxol-4-yl)borane, while cooling with ice, 35 ml of 3N sodium hydroxide solution, immediately followed by the addition, over a period of 10 minutes, of 32 ml (~310 mmol) of 30% hydrogen peroxide solution. The yellow-orange emulsion is adjusted to pH 3 with 10% HCl. The aqueous phase is extracted three times with 150 ml of diethyl ether each time. The organic solutions are washed three times with 100 ml of 2N FeSO$_4$ solution each time, then twice with 100 ml of 20% sodium bisulfite solution each time and finally with 50 ml of brine, dried over MgSO$_4$ and concentrated in a vacuum rotary evaporator. Upon distillation of the residue, 8.4 g (48%) of the product distil over in the form of a pale yellow oil at boiling point (b.p.) 135°–139° C./25 mbar.

$^1$H-NMR (CDCl$_3$; 300 MHz): 6.93 (t; J 8.1; 1H); 6.67 (d×d; J 8.1; 1.0; 1H); 6.64 (d×d; J 8.1; 1.0; 1H); 6.15 (bs; OH).

EXAMPLE 9

Preparation of 2,2-difluoro-1,3-benzodioxole-4-boric acid 7.9 g (50 mmol) of 2,2-difluoro-1,3-benzodioxole are metallated according to Example 1, at −70° C., with 40 ml of tert.-butyllithium (1.38M in pentane) in a mixture of 55 ml of diethyl ether and 30 ml of THF. 5.1 g (50 mmol) of trimethyl borate in 25 ml of diethyl ether are then added to the aryllithium compound at −100° C. over a period of 2 minutes. The clear, yellow reaction solution is then allowed to warm up to room temperature and, after being stirred for 30 minutes while cooling with ice, is hydrolysed with 100 ml of 2N HCl. The aqueous phase is extracted three times with 75 ml of diethyl ether each time. The organic solutions are washed neutral with water and brine and, without being dried, are concentrated in a vacuum rotary evaporator. The yellow crystalline residue is recrystallised from petroleum ether. 7.4 g (73%) of pale yellow prisms of melting point (m.p.) 103°–104° C. are obtained.

$^1$H-NMR (CDCl$_3$; 300 MHz); 7.51 (m; X of ABX; 1H); 7.18 (m; AB of ABX; 2H); 5.33 (bs; 2×OH).

EXAMPLE 10

Preparation of 2,2-difluoro-1,3-benzodioxole-4-thiophenol 4.8 g (30 mmol) of 2,2-difluoro-1,3-benzodioxole are metallated as described in Example 1 with 24 ml (33 mmol) of tert.-butyllithium (1.38M in pentane) in a mixture of 35 ml of THF and 15 ml of diethyl ether. 1.1 g (34 mmol) of sulfur (S$_8$) are then added in portions, at −30° C., over a period of 10 minutes. The orange reaction solution is subsequently maintained at −30° C. for a further 20 minutes and is then hydrolysed with 30 ml of 2N HCl. The aqueous phase is extracted twice with 50 ml of diethyl ether each time. The organic phases are washed neutral with water and brine, dried over MgSO$_4$ and concentrated in a vacuum rotary evaporator. Fractional distillation of the residue yields 3.4 g (60%) of colourless product of boiling point (b.p.) 72°–74° C./20 mbar.

$^1$H-NMR (CDCl$_3$; 60 MHz): 6.85 (m; 3H); 3.49 (s, SH).

EXAMPLE 11

Preparation of 4-(chlorodifluoroacetyl)-2,2-difluoro-1,3-benzodioxole 39.5 g (250 mmol) of 2,2-difluoro-1,3-benzodioxole are metallated according to Example 2, at −15° C., with 172 ml (275 mmol) of n-butyllithium (1.60M in hexane) and 32 g (275 mmol) of TMEDA in 300 ml of hexane. To the precipitated 2,2-difluoro-1,3-benzodioxol-4-yllithium, a solution of 50.0 g (250 mmol) of α-chloro-α,α-difluoroacetylmorpholide in 100 ml of THF is added at −15° C. over a period of 40 minutes during which a voluminous white precipitate gradually forms. The suspension is stirred at 0° C. for 1 hour, then hydrolysed with 120 ml of 10% HCl. The aqueous phase is extracted twice with 250 ml of diethyl ether each time. The organic solutions are washed twice with 100 ml of 1N HCl each time, dried over MgSO$_4$ and concentrated at 50° C. in a vacuum rotary evaporator. Fractional distillation yields 41.3 g (61%) of a pale yellow product of boiling point (b.p.) 93°–95° C./25 mbar.

$^1$H-NMR (CDCl$_3$; 300 MHz): 7.75 (d×d; J 8.0; 1.0; 1H); 7.39 (d×d; J 8.0; 1.0; 1H); 7.27 (t; J 8.0).

EXAMPLE 12

The procedure of Example 1 is followed except that trimethylchlorosilane is used instead of trifluoroacetyl-N-methylpiperazide. 4-Trimethylsilyl-2,2-difluoro-1,3-benzodioxole (b.p. 80°–81° C./160 mbar) is obtained in a yield of 73%.

$^1$H-NMR (CDCl$_3$; 300 MHz); 7.09 (m; X of ABX); 7.05 (m; AB of ABX; 2H); 0.33 (s; 9H).

EXAMPLE 13

Preparation of 2,2-difluoro-1,3-benzodioxol-4-yl-lithium a) First 13 g (110 mmol) of N,N,N',N'-tetramethylethylenediamine in 30 ml of toluene/tetrahydrofuran (2:1) and then 15.8 g (100 mmol) of 2,2-difluoro-1,3-benzodioxole, dissolved in 120 ml of toluene/tetrahydrofuran (2:1), are added dropwise under a nitrogen atmosphere at from −15° to −10° C. to 69 ml (110 mmol) of n-butyllithium (1.6 molar suspension in toluene), n-butane being formed.

A specimen of the resulting dissolved product of formula VII is identified by NMR spectroscopy.

Signals δ ppm: 6.83 d(J=7 Hz) corresponds to: H 7 7.10 dd (J=7 Hz) corresponds to: H 6 7.80 d (J=4 Hz) corresponds to: H 5 b) 94.0 g (272 mmol) of n-butyllithium (18.5% in toluene) are added dropwise under a nitrogen atmosphere at from −15° to −10° C. to 29.5 g (254 mmol) of N,N,N',N'-tetramethylethylenediamine and 40.0 g (253 mmol) of 2,2-difluoro-1,3-benzodioxole in 35 ml of toluene, n-butane being formed in addition to the title compound.

c) 39.3 g (339 mmol) of N,N,N',N'-tetramethylethylenediamine are added dropwise under a nitrogen atmosphere at from −15° to −10° C. to 137.8 g (409 mmol) of n-butyllithium solution (19.0% in toluene). The resulting reaction mixture is added dropwise at from −15° to −10° C. under a nitrogen atmosphere to a solution of 53.3 g (337 mmol) of 2,2-difluoro-1,3-benzodioxole in 46 ml of toluene, n-butane being formed in addition to the title compound.

The following compounds of formula VII are prepared analogously to Example 1.

TABLE

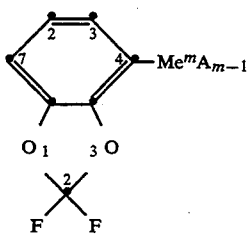

(VII)

Compounds of formula VII

| compound no. | Me | Y | NMR: δ (ppm) | position H atom |
|---|---|---|---|---|
| 1 | Li | — | 6,83(d)(J=7Hz) | 7 |
|   |    |   | 7,10(dd)(J=7Hz) | 6 |
|   |    |   | 7,80(d)(J=4Hz) | 5 |
| 2 | Na | — |   |   |
| 3 | K  | — | 6,85(d)(J=7Hz) | 7 |
|   |    |   | 7,05(dd)(J=7Hz) | 6 |
|   |    |   | 7,76(d)(J=4Hz) | 5 |
| 4 | Cs | Cl⁻ |   |   |
| 5 | Mg | Br⁻ | 6,86(d)(J=7Hz) | 7 |
|   |    |   | 6,65(dd)(J=7Hz) | 6 |
|   |    |   | 7,42(d)(J=4Hz) | 5 |
| 6 | Hg | Cl⁻ | 6,93(d)(J=7Hz) | 7 |
|   |    |   | 6,84(dd)(J=7Hz) | 6 |
|   |    |   | 7,05(d)(J=4Hz) | 5 |
| 7 | Zn | Cl⁻ | 6,84(d)(J=7Hz) | 7 |
|   |    |   | 6,98(dd)(J=7Hz) | 6 |
|   |    |   | 7,14(d)(J=4Hz) | 5 |
| 8 | Cu | Cl⁻ |   |   |

EXAMPLE 14

Preparation of 3-(2,2-difluorobenzodioxol-4-yl)-4-cyanopyrrole a) First 48.2 g of N,N,N',N'-tetramethylethylenediamine, and then, after stirring for 30 minutes, 60 g of 2,2-difluoro-1,3-benzodioxole dissolved in 200 ml of hexane are added under an inert gas atmosphere at −20° to 261 ml of 1.6N n-butyllithium in hexane. After 15 minutes, 70.7 g of ethoxymethylenecyanoacetic acid ethyl ester dissolved in 250 ml of tetrahydrofuran are added at −15° within a period of 25 minutes. After a further 30 minutes, 81.5 g of p-toluenesulfonylmethyl isocyanide dissolved in 220 ml of tetrahydrofuran are added to the resulting suspension at 0° over a period of 25 minutes. The solution is then heated to 25° and 400 ml of solvent are evaporated off in vacuo.

The residue is diluted with 500 ml of ethyl acetate and the resulting solution is washed twice with 300 ml of water and twice with 300 ml of saturated sodium chloride solution and dried over magnesium sulfate. The solvent is evaporated off in vacuo.

The residue is chromatographed over silica gel using hexane/ethyl acetate (3:1) as eluant.

After evaporation of the solvent in vacuo, the title compound having a melting point of 193°–195° C. is obtained. Yield 70% of the theoretical yield, based on 2,2-difluorobenzo-1,3-dioxole.

b) 106.2 g (307 mmol) of n-butyllithium solution (18.5% in toluene) are added dropwise under a nitrogen atmosphere at from −15° to −10° C. to 29.5 g (254 mmol) of N,N,N',N'-tetramethylethylenediamine and 40 g (253 mmol) of 2,2-difluoro-1,3-benzodioxole in 35 ml of toluene. 52.1 g (308 mmol) of ethoxymethylenecyanoacetic acid ethyl ester in 115 ml of toluene are then added within a period of 2 hours at from −15° to −10° C. After 20 minutes, the resulting suspension is heated to 0° C. and 50 g (256 mmol) of p-toluenesulfonylmethyl isocyanide dissolved in 135 ml of tetrahydrofuran are added over a period of 30 minutes. The reaction mixture is then heated to 25° C., added to 150 ml of water and filtered to obtain the title compound.

c) 39.3 g (339 mmol) of N,N,N',N'-tetramethylethylenediamine are added dropwise under a nitrogen atmosphere at from −15° to −10° C. to 137.8 g (409 mmol) of n-butyllithium solution (19.0% in toluene). The resulting reaction mixture is metered at from −15° to −10° C. under a nitrogen atmosphere into a solution of 53.3 g (337 mmol) of 2,2-difluorobenzo-2,3-dioxole in 46 ml of toluene. 69.1 g (409 mmol) of ethoxymethylenecyanoacetic acid ethyl ester in 150 ml of toluene are then metered in at from −15° to −10° C. The resulting suspension is subsequently heated to 0° C. and 66.6 g (342 mmol) of p-toluenesulfonylmethyl isocyanide dissolved in 180 ml of tetrahydrofuran are added. The reaction mixture is then heated to 25° C., added to 200 ml of water and filtered to obtain the title compound.

What is claimed is:

1. A process for the preparation of a compound of formula I

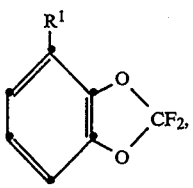

(I)

wherein R¹ is —OH, —SH, —CHO, —CN, —COOH, —B(OH)₂, —COX, with X being Cl or Br, or is —COOR², —SiR₃² or —B(OR²)₂, with R² being a C₁-C₁₂alcohol moiety without the hydroxy group, wherein R¹ is further —C$_n$H$_{2n}$COOR², with n being an integer from 1 to 4, or linear or branched C₁-C₁₂hydroxyalkyl which is unsubstituted or is substituted by —F, —CN, C₁-C₆alkoxy, phenyl, fluorophenyl, C₁-C₄alkoxy-phenyl, C₁-C₄alkylthio-phenyl, C₁-C₄alkylphenyl, C₁-C₄fluoroalkyl-phenyl, nitrophenyl or by cyanophenyl, or wherein R¹ is a benzyl alcohol or a C₁-C₁₂acyl moiety, each unsubstituted or substituted by F, C₁-C₄alkoxy, C₁-C₄alkylthio, C₁-C₄alkyl, C₁-C₄fluoroalkyl, nitro or by cyano, or wherein R¹ is a radical of formula II

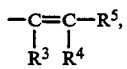

(II)

wherein R⁵ is —CN, —CF₃, —COOR², —CONH₂, —CO—NHR² or —CONR₂², R³ and R⁴ are a direct bond or each is H, or R³ is H and R⁴ independently has the meanings of R⁵, which process comprises a) in an inert solvent, reacting 2,2-difluorobenzo-1,3-dioxole with an alkali metal compound with a strong anion base to give a compound of formula IV

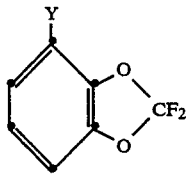

(IV)

wherein Y is an alkali metal, and optionally then reacting with an anhydrous metal halide from the group MgZ₂, ZnZ₂, CdZ₂, CuZ, CuZ₂, PdZ₂, NiZ₂, AlZ₃, SiZ₄, SnZ₂, SnZ₄, TiZ₄, BZ₃ or ZrZ₄ to give a compound of formula IV wherein Y is —Cu, —MgZ, —ZnZ, —CdZ, —CuZ, —PdZ, —NiZ, —AlZ₂, —SiZ₃, SnZ, —SnZ₃, TiZ₃, —BZ₂ or —ZrZ₃ and Z is —Cl, —Br or —I and, in the case of boron, is also —OC₁-C₄alkyl or —O—aryl, b) reacting the compound of formula IV with an electrophilic compound from the group X—CN, CO₂, S₈, COX₂, B(OR²)₃, X—SIR₃², R²O—SiR₃² or XCOOR², with X being —Cl or —Br, or with a formylating reagent, CH₂O, an epoxide, a benzaldehyde which is unsubstituted or is substituted by F, C₁-C₄alkoxy, C₁-C₄alkylthio, C₁-C₄alkyl, C₁-C₄fluoroalkyl, nitro or by cyano, a C₁-C₁₁alkyl-CHO which is unsubstituted or is substituted by —F, —Cl, —CN, C₁-C₆alkoxy, phenyl, fluorophenyl, C₁-C₄alkoxyphenyl, C₁-C₄-alkylthiophenyl, C₁-C₄alkylphenyl, C₁-C₄fluoroalkylphenyl, nitrophenyl or by cyanophenyl, or with C₁-C₁₂acyl-X¹ or C₁-C₁₂fluoroacyl-X¹, wherein X¹ is —Cl, —Br, C₁-C₆alkoxy or the radical of a secondary amine, or with X²C$_n$H$_{2n}$COOR², X²—CR³=CR⁴R⁵ wherein X² is a leaving group, and c) isolating the compound of formula I or first hydrolysing the reaction mixture and then isolating the compound of formula I.

2. A process for the preparation of a compound of formula I according to claim 1, wherein R¹ is —CHO, —CN, —COOH, —B(OH)₂, —COX, with X being Cl or Br, or is —COOR² or —B(OR²)₂, with R² being a C₁-C₁₂alcohol moiety without the hydroxy group, wherein R¹ is further —C$_n$H$_{2n}$COOR², with n being an integer from 1 to 4, or linear or branced C₁-C₁₂hydroxyalkyl or C₁-C₁₂acyl each unsubstituted or substituted by —F, —CN, C₁-C₆alkoxy, phenyl, fluorophenyl, C₁-C₄alkoxyphenyl, C₁-C₄alkylthiophenyl, C₁-C₄alkylphenyl, C₁-C₄fluoroalkylphenyl, nitrophenyl or by cyanophenyl, or wherein R¹ is a radical of formula II

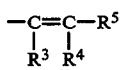

(II)

wherein R⁵ is —CN, —CF₃, —COOR², —CONH₂, —CO—NHR² or —CONR₂², R³ and R⁴ are a direct bond or each is H, or R³ is H and R⁴ independently has the meanings of R⁵, which process comprises a) in an inert solvent, reacting 2,2-difluorobenzo-1,3-dioxole with an alkali metal compound with a strong anion base to give a compound of formula IV

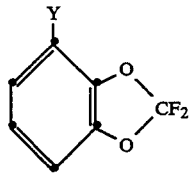

(IV)

wherein Y is an alkali metal, and optionally then reacting with an anhydrous metal halide from the group MgZ₂, ZnZ₂, CdZ₂, CuZ, CuZ₂, PdZ₂, NiZ₂, AlZ₃, SiZ₄, SnZ₂, SnZ₄, TiZ₄, BZ₃ or ZrZ₄ to give a compound of formula IV wherein Y is —Cu, —MgZ, —ZnZ, —CdZ, —CuZ, —PdZ, —NiZ, —AlZ₂, —SiZ₃, —SnZ, —SnZ₃, —TiZ₃, —BZ₂ or —ZrZ₃ and Z is —Cl, —Br or —I and, in the case of boron, is also —OC₁-C₄alkyl, b) reacting the compound of formula IV with an electrophilic compound from the group X—CN, CO₂, B(OR²)₃, COX₂ or XCOOR², with X being —Cl or —Br, or with a formylating reagent, CH₂O, an epoxide, a C₁-C₁₁alkyl-CHO which is unsubstituted or is substituted by —F, —Cl, —CN, C₁-C₆-alkoxy, phenyl, fluorophenyl, C₁-C₄alkoxyphenyl, C₁-C₄-alkylthiophenyl, C₁-C₄-alkylphenyl, C₁-C₄fluoroalkylphenyl, nitrophenyl or by cyanophenyl, or with C₁-C₁₂acyl-X¹ wherein X¹ is —Cl, —Br, C₁-C₆alkoxy or the radical of a secondary amine, or with X²C$_n$H$_{2n}$COOR², X²—CR³=CR⁴R⁵ wherein $X^2$ is a leaving group, and c) isolating the compound of formula I or first hydrolysing the reaction mixture and then isolating the compound of formula I.

3. A process for the preparation of a compound of formula I according to claim 2,

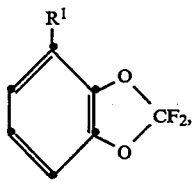
(I)

wherein $R^1$ is —CHO, —CN, —COOH, —COX, with X being Cl or Br, —COOR$^2$, with $R^2$ being a $C_1$-$C_{12}$alcohol moiety without the hydroxy group, —$C_nH_{2n}$COOR$^2$, with n being an integer from 1 to 4, linear or branched $C_1$-$C_{12}$hydroxyalkyl or $C_1$-$C_{12}$acyl each unsubstituted or substituted by —F, —CN, $C_1$-$C_6$alkoxy, phenyl, fluorophenyl, $C_1$-$C_4$alkoxyphenyl, $C_1$-$C_4$alkylthiophenyl, $C_1$-$C_4$alkylphenyl, $C_1$-$C_4$fluoroalkylphenyl, nitrophenyl or by cyanophenyl, or is a radical or formula

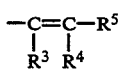
(II)

wherein $R^5$ is —CN, —CF$_3$, —COOR$^2$ or —CONR$_2^2$, $R^3$ and $R^4$ are a direct bond or each is H, or $R^3$ is H and $R^4$ independently has the meanings of $R^5$,
which process comprises a) in an inert solvent, reacting 2,2-difluorobenzo-1,3-dioxole with an alkali metal compound with a strong anion base to give a compound of formula IV

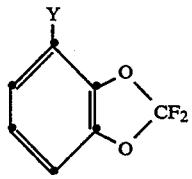
(IV)

wherein Y is an alkali metal, and optionally then reacting with an anhydrous metal halide from the group MgZ$_2$, ZnZ$_2$, CdZ$_2$, CuZ, CuZ$_2$, PdZ$_2$, NiZ$_2$, AlZ$_3$, SiZ$_4$, SnZ$_2$, SnZ$_4$, TiZ$_4$ or ZrZ$_4$ to give a compound of formula IV wherein Y is —Cu, —MgZ, —ZnZ, —CdZ, —CuZ, —PdZ, —NiZ, —AlZ$_2$, —SiZ$_3$, —SnZ, —SnZ$_3$, —TiZ$_3$ or —ZrZ$_3$ and Z is —Cl, —Br or —I, b) reacting the compound of formula IV with an electrophilic compound from the group X—CN, CO$_2$, COX$_2$ or XCOOR$^2$, with X being —Cl or —Br, or with a formylating reagent, CH$_2$O, a $C_1$-$C_{11}$alkyl-CHO which is unsubstituted or is substituted by —F, —CN, $C_1$-$C_6$alkoxy, phenyl, fluorophenyl, $C_1$-$C_4$alkoxyphenyl, $C_1$-$C_4$alkylthiophenyl, $C_1$-$C_4$alkylphenyl, $C_1$-$C_4$fluoroalkylphenyl, nitrophenyl or by cyanophenyl, an epoxide, a benzaldehyde which is unsubstituted or is substituted by —F, $C_1$-$C_4$alkoxy, $C_1$-$C_4$alkylthio, $C_1$-$C_4$alkyl, $C_1$-$C_4$fluoroalkyl, nitro or by cyano, or with $C_1$-$C_{12}$acyl-X$^1$ wherein X$^1$ is —Cl, —Br, $C_1$-$C_6$alkoxy or the radical of a secondary amine, or with $X^2C_nH_{2n}COOR^2$, $X^2$—CR$^3$=CR$^4$R$^5$ wherein $X^2$ is a leaving group, and c) isolating the compound of formula I or first hydrolysing the reaction mixture and then isolating the compound of formula I.

4. A process for the preparation of a compound of formula I according to claim 3,

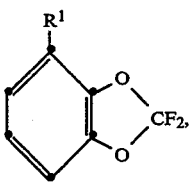
(I)

wherein $R^1$ is —CHO or a radical of formula II

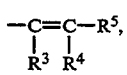
(II)

wherein $R^5$ is —CN, —COOR$^2$ or —CONH$_2$, each of $R^3$ and $R^4$ is H, or $R^3$ is H and $R^4$ independently has the meanings of $R^5$.

5. A process for the preparation of 2,2-difluoro-1,3-benzodioxol-4-yl-carbaldehyde of the formula

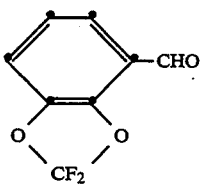

according to claim 4.

6. A process according to claim 3, wherein the reaction is carried out at from −150° C. to 150° C.

7. A process according to claim 6, wherein the reaction is carried out at from −30° C. to +10° C.

8. A process according to claim 5, wherein the reaction is carried out with butyllithium as metallating reagent, in the presence of a complex-forming compound at from −15° C. to +10° C.

9. A process according to claim 3, wherein the solvent is a non-polar or polar aprotic solvent.

10. A process according to claim 3, wherein the reaction mixture contains, in addition, a complexing agent.

11. A process according to claim 3, wherein the alkali metal compound is a Li-, Na-, K-, -alkyl, -amide or -alcoholate.

12. A process according to claim 11, wherein the alkali metal is Li.

13. A process according to claim 5, wherein the formylating reagent is a formic acid ester, an orthoformic acid ester, an alkoxymethyleneaniline or an N-disubstituted formamide.

14. A process according to claim 13, wherein the formylating reagent is dimethyl formamide.

15. A process according to claim 3, wherein, as the radical of a secondary amine, X$^1$ is

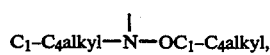

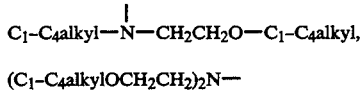

$(C_1-C_4alkylOCH_2CH_2)_2N-$ or the radical of a 5- or 6-membered heterocyclic amine which may contain a further hetero atom from the group —O— and =N—$C_1$-$C_4$alkyl.

16. A process according to claim 3, wherein $X^2$ is a leaving group is a halide, $C_1$-$C_6$alkoxy, $C_6$-$C_{10}$aryloxy, $C_1$-$C_{12}$-secondary amino, $C_1$-$C_8$acyloxy or the radical of a sulfonic acid.

17. A process according to claim 8, wherein the complex-forming compound is selected from a group consisting of ethers, tert.-amines, cyclic ureas and N-substituted acid amides.

18. A process according to claim 17, wherein the complex-forming compound is selected from a group consisting of ethylene glycol dimethyl ether, hexamethylphosphoric acid triamide, 1,3-dimethyl-2-imidazolone, dimethylethyleneurea, dimethylpropyleneurea and N,N,N',N'-tetramethylethylenediamine, and an organolithium compound is used as the metal compound.

19. A process according to claim 18, wherein a suspension of n-butyllithium is reacted with the equivalent amount of tetramethylethylenediamine at −15° to −10° C., and the resulting reaction mixture is added to 2,2-difluoro-1,3-benzodioxole at a maximum molar ratio of n-butyllithium to 2,2-difluoro-1,3-benzodioxole of 0.99 to 1.02 in an inert solvent and the reaction mixture is reacted in succession by adding an equivalent amount of dimethyl formamide to the reaction mixture, by hydrolysing the reaction mixture, and the reaction product is isolated.

20. A process according to claim 18, wherein a suspension of n-butyllithium is added at −15° C. to −10° C. to a solution of 2,2-difluoro-1,3-benzodioxole and of the approximately equimolar amount of tetramethylethylenediamine at a maximum molar ratio of n-butyllithium to 2,2-difluoro-1,3-benzodioxole of 0.99 to 1.02, in an inert solvent and the reaction mixture is reacted in succession by adding an equivalent amount of dimethyl formamide to the reaction mixture, by hydrolysing the reaction mixture, and the reaction product is isolated.

21. A process according to claim 18, wherein s suspension of n-butyllithium is continuously fed into a prepared solution of difluoro-1,3-benzodioxole and of tetramethylethylenediamine at a maximum molar ratio of n-butyllithium to 2,2-difluoro-1,3-benzodioxole of 0.99 to 1.02, at −5° to +10° C., in an inert solvent and the reaction mixture is immediately and continuously reacted with dimethyl formamide and hydrolised, and the reaction product is isolated.

* * * * *